United States Patent

Martin et al.

Patent Number: 5,552,508
Date of Patent: Sep. 3, 1996

[54] DIFUNCTIONAL BITRICYCLODECATRIENE MONOMERS

[75] Inventors: David C. Martin, Ann Arbor, Mich.; Jeffrey S. Moore, Savoy, Ill.; Larry J. Markoski, Ypsilanti, Mich.; Kenneth A. Walker, Urbana, Ill.; Gary E. Spilman, Ann Arbor, Mich.

[73] Assignee: University of Michigan, The Board of Regents, Ann Arbor, Mich.

[21] Appl. No.: 448,637

[22] Filed: May 23, 1995

Related U.S. Application Data

[60] Continuation-in-part of Ser. No. 284,006, Aug. 1, 1994, Pat. No. 5,418,312, which is a division of Ser. No. 907,430, Jul. 1, 1992, Pat. No. 5,334,752.

[51] Int. Cl.$^6$ ............................................. C08G 63/00
[52] U.S. Cl. .................... 528/68; 528/74; 528/125; 528/128; 528/190; 528/206; 528/212; 528/219; 528/271; 528/298; 528/332; 528/339; 528/344
[58] Field of Search ............................. 528/68, 74, 125, 528/128, 190, 206, 212, 219, 271, 298, 332, 339, 344

[56] References Cited

U.S. PATENT DOCUMENTS 5,418,312  5/1995  Martin et al. ........................... 528/68

OTHER PUBLICATIONS

Chemical Abstracts 110:23473, "Cyclobutarenes", Michael K. Shepard.

Primary Examiner—Frederick Krass
Attorney, Agent, or Firm—Rohm & Monsanto

[57] ABSTRACT

Novel difunctionalized cyclobutabenzene monomers of the general formula:

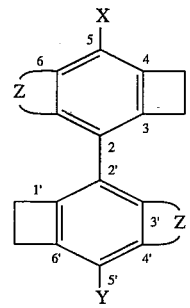

wherein Z can be hydrogens or a cyclobutane ring; and X and Y are carboxyl, amino, alcohol, isocyanate, acid halide, or bis-acyl halide groups. Exemplary difunctional bitricyclodecatriene monomers are [2,2'-bidicyclo[2.4.0]octa-1,3,5-triene]-5,5'-dicarboxylic acid (BXTA) and [2,2'-bitricyclo[6.2.0.0]deca-1,3,(6),7-triene]-7,7'- dicarboxylic acid (QXTA). The difunctionalized bitricyclodecatriene monomers can form part of a polymer backbone chain in which the multiple butane ring functionalities can be easily opened to produce strong, three-dimensional covalent bond crosslinking between polymer chains. The crosslinking can be induced simply by heating the polymer to a temperature in excess of 250° C.

6 Claims, 11 Drawing Sheets

SCHEME I

SCHEME II

DIFFRACTION ANGLE

DIFUNCTIONAL BITRICYCLODECATRIENE MONOMERS

GOVERNMENT RIGHTS

This invention was made under contract awarded by United States Army Advanced Concepts Technology Committee, Contract Number DAAK60-92-K-0005. The government of the United States has certain rights in the invention.

CROSS-REFERENCE TO RELATED APPLICATIONS

This application is a continuation-in-part of U.S. Ser. No. 08/284,006 filed on Aug. 1, 1994, now U.S. Pat. No. 5,418,312, which was a division of U.S. Ser. No. 07/907,430 filed on Jul. 1, 1992, now U.S. Pat. No. 5,334,752, both applications being assigned to the assignee hereof. The disclosures of these applications are hereby incorporated by reference.

BACKGROUND OF THE INVENTION

1. Technical Field

This invention relates generally to novel cyclobutabenzene derivatives, and more particularly, to difunctionalized bitricyclodecatriene monomers which are derived from 3,6-functionalized mono- and dicyclobutabenzene compounds of the type disclosed in the above-referenced patents.

2. Background of the Prior Art

Recently, much effort has been expended toward producing high performance engineering thermoplastics with improved polymer microstructure in order to achieve specific desired polymer properties, such as strength; stiffness, long term dimensional stability, or acid/high temperature resistance. Some of this effort has been directed to incorporating cyclobutabenzene groups into known polymers.

The cyclobutabenzenes are useful because of a crosslinking reaction which can be thermally triggered resulting in ring-opening of cyclobutabenzene (BCB) to form the highly reactive o-quinodimethane intermediate at temperatures above 300° C.:

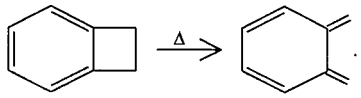

The o-quinodimethane intermediate is sufficiently reactive to homopolymerize through an addition reaction or by Diels-Alder dimerization. In either case, crosslinking should take place with little or no mass loss as the cyclobutane ting unfurls.

Previous use of the BCB functionality in polymer chemistry has been limited to structoterminal prepolymers (i.e., oligomers endcapped with BCB). When the BCB functionality is used as an end-group in a polymer molecule, crosslinking occurs only at the end of the polymer molecules, and therefore, the degree of crosslinking is inversely related to the molecular weight. When BCB functionalities are placed as a reactive pendant groups along the polymer backbone, the degree of crosslinking can be controlled. However, the resulting crosslinks are flexible and are not very ordered. This can lead to a lower modulus and disruption of crystallinity in the polymer, and hence, lower performance of polymer properties. Moreover, in both cases, the crosslinking function must be performed after polymerization is complete.

These approaches, therefore, suffered from limited processability and limited ability to vary crosslink density. There is, thus, a need for a structopendant crosslinking group (i.e., a crosslinking group placed directly in the backbone of the polymer as a monomeric unit), such that the reactive crosslinking functionality remains intact for secondary polymerization. This would permit greater control of the extent of crosslinking to achieve high performance polymers having particular desired properties. There is a further need for a structopendant crosslinking group which can be activated for crosslinking at any desired time during the processing, including subsequent to fiber formation, casting, or molding.

In all of the structoterminal prepolymers mentioned above, the aromatic BCB ring was simply monofunctionalized at the 4 position (the product accessible through electrophilic aromatic substitution). There is a need in the art for difunctionalized cyclobutabenzene derivatives which can be used as structopendant crosslinking groups. One obstacle encountered in incorporating the BCB functionality into the backbone of a polymer has been the difficulty in producing regioselective difunctionalization of the cyclobutabenzene unit. There is, therefore, a need for a method for regioselectively introducing a difunctionality onto the 3 and 6 positions of cyclobutabenzene.

Terephthalic acid (TA) is a difunctionalized monomer, for example, which is widely used in the production of high-performance aromatic polymers such as Poly{(benzo-[1,2-d; 4,5-d']-bisoxazole-2,6-diyl)- 1,4-phenylene} (PBZT), Poly(p-phenylene terephthalamide) (PPTA or Kevlar®, a trademark of Dupont Chemical Company, Wilmington, Del.), and Poly(ethylene terephthalate) (PET). PPTA, PBZO, and PBZT, for example, are present state-of-the-art polymer materials for lightweight structural applications. Although these materials are strong and stiff, they are disadvantageously relatively weak in compression. The compression failure occurs by strain localization into well-defined kink bands. Detailed structural investigation of the kink bands using High Resolution Electron Microscopy revealed that both chain slip and chain bending or breaking are involved in this deformation mode.

PPTA, PBZO and PBZT are all bonded laterally in the solid state by weak secondary forces. There is a need in the art for a means of providing strong, covalent lateral crosslinks between the polymer molecules in these high-performance polymers to further improve their mechanical properties. There is, thus, a need in the art for an analog of TA which has an additional functionality having the ability to produce such strong, covalent crosslinks between polymer chains. There is a further need in the art for an analog of TA which can advantageously be substituted therefor to improve polymer properties without modifying existing processes.

The monomers disclosed in U.S. Pat. Nos. 5,418,430 and 5,334,752 have structopendant crosslinking groups and address some of the problems in the prior art. U.S. Pat. Nos. 5,4 18,430 and 5,334,752 cover reactive difunctionalized monomers of 1,2-dihydrocyclobutabenzene (BCB) and 1,2, 4,5-dicyclobutabenzene (DBCB), such as 1,2,-dihydrocyclobutabenzene- 3,6-carboxylic acid (XTA) or [6.2.0.0] deca-1,3,7-triene-7,7'-dicarboxylic acid (DXTA) which are improved analogs of TA. While the use of XTA or DXTA in copolymers with PPTA, for example, results in polymers having improved material properties such as strength, modulus, toughness, and flame resistance. There is still a need for 3,6-difunctionalized monomers having an improved density of crosslinkable groups, or crosslinkable groups which will result in polymers having improved orientation and higher dimensionality.

It is, therefore, an object of this invention to provide difunctionalized cyclobutabenzene monomers and methods of making same.

It is a further object of the invention to provide difunctional cyclobutabenzene monomers which are difunctional bitricyclodecatriene monomers.

It is another object of the invention to provide difunctionalized cyclobutabenzene monomers which can be substituted for existing corresponding monomers in existing polymers without substantially modifying the existing processes.

It is also an object of this invention to provide difunctionalized cyclobutabenzene monomers for controlled incorporation of a cyclobutane functionality into a polymer backbone to yield polymers of improved mechanical compressive strength and well as other improved properties.

It is still a further object of the invention to provide a method for regioselectively introducing a difunctionality onto the 3 and 6 positions of a cyclobutabenzene.

SUMMARY OF THE INVENTION

The foregoing and other objects are achieved by this invention which provides difunctionalized cyclobutabenzene monomers having a disubstituted benzene ring to which one or more unsubstituted cyclobutane rings are fused. The difunctionalized cyclobutabenzene monomers have the general formula I:

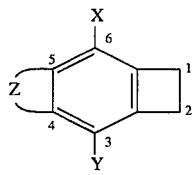

where Z is hydrogens or a cyclobutane ring. The X and Y substituents, which may be the same or different, are —COOH, —NH$_2$, —OH, —COCl, —NCO, or bis acyl halide, such as chloride or fluoride. The ring positions have been numbered for nomenclature purposes.

The X/Y substituents are chosen so that the cyclobutabenzene participates as a monomer in a primary polymerization reaction via the substituent functionalities so that the cyclobutabenzene is a component of the polymeric backbone. Thus, the cyclobutane functionality is available for secondary polymerization, or crosslinking, to produce strong, covalent bonds between polymer chains.

In particular preferred embodiments, the cyclobutabenzene derivatives are 1,2-dihydrocyclobutabenzene- 3,6-carboxylic acid; 1,2-dihydrocyclobutabenzene-3,6-diamine; 1,2-dihydrocyciobutabenzene-3,6-isocyanate; 1,2-dihydrocyclobutabenzene-3,6-acid halide; and 3,6-hydroxy-1,2-dihydrocyclobutabenzene.

In a further embodiment of the invention, the difunctionalized cyclobutabenzene monomers are a disubstituted bitricyclodecatriene having the general formula II:

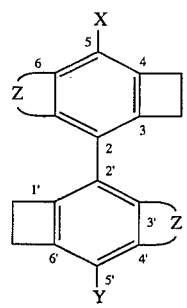

where Z is hydrogens or a cyclobutane ring. The X and Y substituents, which may be the same or different, are —COOH, —NH$_2$, —OH, —COCl, —NCO, or bis acyl halide, such as chloride or fluoride, as in the compounds of general formula I. The ring positions have been numbered for nomenclature purposes.

In particular preferred embodiments, the difunctional bitricyclodecatriene monomers are [2,2'-bidicyclo[2.4.0] octa-1,3,5-triene]-5,5'-dicarboxylic acid (BXTA) and [2,2'-bitricyclo[6.2.0.0]deca-1,3,(6),7-triene]-7,7'- dicarboxylic acid (QXTA). The higher order reactivity of the biphenyl species will provide three-dimensional strengthening in a later high-temperature processing step.

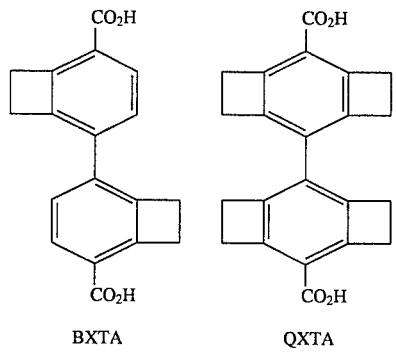

BXTA          QXTA

Of course, other disubstituted bitricyclodecatriene monomers within the specific contemplation of the invention include [2,2'-bidicyclo[2.4.0]octa-1,3,5-triene]-5,5'-diamine; [2,2'-bidicyclo[2.4.0]octa-1,3,5-triene]- 5,5'-dialcobol; [2,2'-bidicyclo[2.4.0]octa-1,3,5-triene]-5,5'-diisocyanate; [2,2'-bidicyclo[2.4.0]octa-1,3,5-triene]-5,5'-diacid halide;[2,2 '-bidicyclo[2.4.0]octa-1,3,5-triene]-5,5'-di(4-fluorobenzoyl); [2,2'-bitricyclo[6.2.0.0]deca-1,3,(6),7-triene]-7,7'-diamine; [2,2'-bitricyclo[6.2.0.0]deca-1,3,(6),7-triene]-7,7'-dialcohol;[2,2'-bitricyclo[6.2.0.0]deca-1,3,(6), 7-triene]- 7,7'-diisocyanate; 2,2'-bitricyclio[62.0.0]deca-1,3, (6),7-triene]- 7,7'-diacid halide; and [2,2'-bitricyclo[6.2.0.0] deca-1,3,(6), 7-triene]-7,7'-di(4-flurobenzoyl).

In further embodiments, resins are provided from polymerization of the novel monomers with copolymers which are capable of reacting with the X/Y functionalities of the cyclobutabenzene monomer. Heating the resins, preferably to a temperature in excess of about 250° C. for the difunctional bitricyclodecatriene monomers of general formula II, or in excess of about 300° C. for the difunctionalized cyclobutabenzene monomers of general formula I, at any time during processing, causes crosslinking by disrupting the butane ring.

In an illustrative embodiment, the cyclobutabenzene diacid halide monomer of the present invention is condensed with a diamine which contains at least two carbon atoms between the amino groups to form a polyamide. In another illustrative embodiment, the cyclobutabenzene diisocyanate may be polymerized with a diol of similar structure to the aforementioned diamine to form a polyurethane. These are but two examples of the numerous polymers that can be synthesized using one of more of the cyclobutabenzene derivatives of the present invention.

In specific preferred embodiments, the difunctional bitricyclodecatriene monomers, for example, may be condensed to form homopolymers or copolymers with aromatic diamines, such as PPTA, aliphatic diamines, such as those comprising nylons, and the like.

In a process aspect of the invention, a difunctionalized cyclobutabenzene derivative can be made by:

a) converting cyclobutabenzene to 3,6-ditrimetylsilylcyclobutacyclohexadiene by reductive silylation of as first described by Kundig, et al.;

b) aromatizing 3,6-ditrimetylsilylcyclobutacyclohexadiene to fully saturate the cyclohexadiene ring to form 3,6-ditrimethylsilyl-1,2-dihydrocyclobutabenzene;

c) replacing the trimethylsilyl functionality with a halide to form 3,6-dibromo-1,2-dihydrocyclobutabenzene; and d) converting the dihalide to a 1,2-dihydrocyclobutabenzene-3,6-carboxylate via a palladium catalyzed carbonylation reaction and subsequent hydrolysis of the diester to form 1,2-dihydrocyclobutabenzene- 3,6-carboxy acid.

In an alternative embodiment, the dihalide can be converted to 1,2-dihydrocyclobutabenzene- 3,6-carboxylic acid by a Grignard reaction.

In a further process embodiment, 1,2-dihydrocyclobutabenzene-3,6-carboxylic acid can be converted to the corresponding acid halide using thionyl chloride to form 1,2-dihydrocyclobutabenzene- 3,6-acid chloride.

In a still further process embodiment of the invention, the difunctional bitricyclodecatriene monomers are made by the steps of:

a) converting a cyclobutabenzene monomer to a 3,6-trimetylsilylcyclobutacyclohexadiene;

b) aromatizing the 3,6-trimetylsilylcyclobutacyclohexadiene to fully saturate the cyclohexadiene ring or rings to form a 3,6-trimethylsilyl benzocyclobutene intermediate;

c) replacing one of the trimethylsilyl functionalities on the 3,6-trimethylsilyl benzocyclobutene intermediate with a halide to form an unsymmetrical monobromidemono(trimethysiyl) adduct;

d) coupling the unsymmetrical monobromide-mono(trimethysiyl) adducts in a nickel-catalyzed reaction to form a biphenyl-trimethylsilyl compound; and e) replacing the trimethylsilyl functionalities with a halide to form a biphenyl-dihalide.

In a further process embodiment, the dihalide is converted to the corresponding diester via a palladium catalyzed carbonylation reaction followed by subsequent hydrolysis to the diacid. The diacid can be converted to the corresponding acid halide using thionyl chloride.

BRIEF DESCRIPTION OF THE DRAWINGS

Comprehension of the invention is facilitated by reading the following detailed description, in conjunction with the annexed drawing, in which.

DETAILED DESCRIPTION OF PREFERRED EMBODIMENTS

The following specific examples relate to specific embodiments of the difunctionalized cyclobutabenzene analogs of the present invention, and include illustrative methods for synthesizing same.

In a preferred embodiment, the difunctionalized cyclobutabenzene monomer is a derivative of terephthalic acid (TA), specifically, 1,2-dihydrocyclobutabenzene-3,6-carboxylic acid (herein designated as XTA):

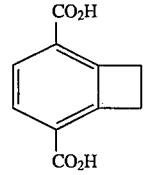

Although XTA is similar in structure to TA, it has an additional functionality, the butane ring, which can be easily opened to produce crosslinking between polymer chains. The crosslinking reaction can be induced simply by heating the polymer to a temperature in excess of 300° C.

In certain preferred embodiments, XTA can be used as a monomer or as a comonomer with TA or its acid chloride analog. By varying the amount of XTA:TA in a polymer reaction, it is possible to systematically tailor the properties of the system to achieve mechanical properties not achievable with either XTA or TA alone. For example, a 1:1 mixture of XTA and TA would yield approximately half the number of BCB groups that the homopolymerization reaction would yield, and thus, would decrease the extent of crosslinking by a factor of two. The extent of crosslinking can be easily controlled by adjusting the ratio of monomers used in the polymerization reaction. Therefore it is possible to significantly alter the mechanical strengths of oriented polymer fibers in compression.

Other structures specifically within the contemplation of the invention include:

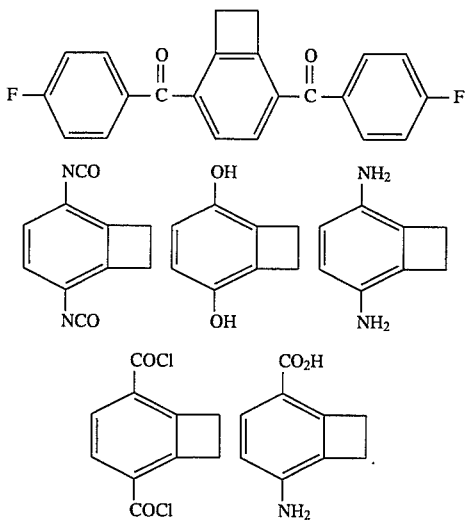

In further embodiments, Z comprises a second cyclobutane ring:

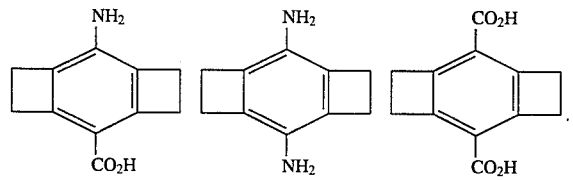

Structures including the second cyclobutane ring increase the possible number of crosslinks by a factor of two and are advantageous for producing a high degree of crosslinking.

Figure 1:
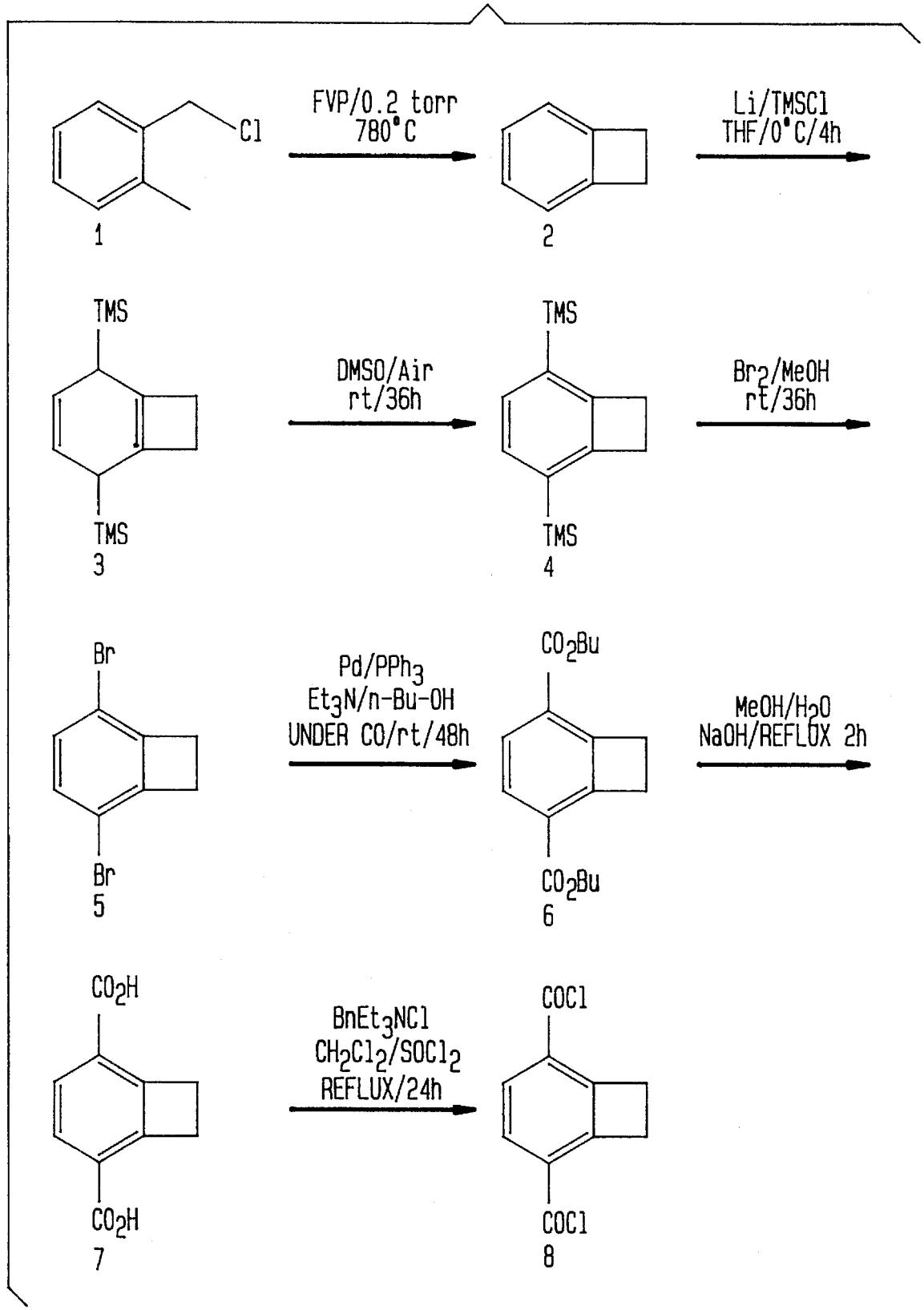
FIG. 1 is an illustrative preparatory scheme for 1,2-dihydrocyclobutabenzene-3,6-carboxylic acid and the corresponding diacid halide.

In a method embodiment of the invention, XTA and its corresponding acid halide are prepared in accordance with the illustrative preparatory scheme outlined in FIG. 1. This preparatory scheme is set forth to demonstrate one successful method of practicing the invention, and in no way is intended to limit the scope of the invention.

1,2-Dihydrocyclobutabenzene (BCB, compound 2):

The starting material, o-toluene-ethyl chloride, (compound 1, 10 g, 71.1 mmol) is degassed to 1 torr and the reaction is run by slow passage of α-chloro-o-xylene through a horizontal quartz tube containing no packing at 780° C. A Kugelrohl bulb in liquid nitrogen is placed at the oven outlet to collect the organic products followed by a second, more efficient trap to collect the HCl gas. This trap system utilizes the large difference in volatility of BCB and HCl to separate these species and thus simplify product workup. The reaction is run successfully over the pressure range of 200–500 mtorr and requires about 30 min for 10 g of starting material. The crude product is taken up in 15% aqueous sodium hydroxide (200 ml) and extracted into pentane (3×200 ml). The entire procedure is repeated ten times. The combined organic layers are washed with saturated sodium chloride solution and analyzed by gas chromatography (GC) to be 88% BCB, 12% starting material, and <1% side reactions (styrene, ethyl benzene). Upon removing solvent, the oil is taken up in dimethylsulfoxide (DMSO; 1 L) with rapid stirring. Excess powdered KOH (20 g) is added to convert the α-chloro-o-xylene to α-hydroxy-o-xylene. This conversion is monitored by GC and is complete within 4 hours. The resulting solution is extracted into water (1 L), adjusted to pH 7, and washed with petroleum ether (3×750 ml). The combined organic layers are dried over anhydrous sodium sulfate and the organic solvent is removed. The resulting brown solution is distilled (65°–68° C. at 20 torr) to yield BCB (compound 2, 63 g, yield: 85%) as a colorless liquid.

3,6-Ditrimethylsilyl-1,2-Dihydrocyclobutabenzene (compound 4)

A dry, magnetically stirred, 500 ml Schlenk flask is charged with a mixture of 57.2 g of lithium dispersion (5% sodium content) in mineral oil and placed under an argon atmosphere. Dry pentane is added via vacuum transfer under rapid stirring to solvate the mineral oil. The pentane/mineral oil solution is removed via filtration under argon. Pentane washing is repeated several times to ensure efficient removal of the mineral oil. The remaining mass of Li metal is determined (14.1 g, 2.03 mol) and the flask is cooled to 0° C. and charged with dry tetrahydrofuran (THF; 500 ml) via cannula transfer. In one portion, chlorotrimethylsilane (187.2 ml, 1.48 tool) is added. BCB (compound 2, 52 g, 500 mmol) is then added dropwise over a period of an hour via syringe to the rapidly stirring solution. The reaction continues for 4 hours and is monitored by GC until complete. Upon completion the mixture is cooled to 0° C. and isopropyl alcohol (100 ml) is added dropwise to carefully quench excess Li. The resulting solution is partitioned into water (1 L) and washed with petroleum ether (3×750 ml). The combined organic layers are dried over anhydrous sodium sulfate and removal of solvent yields a brown oil (compound 3, 114.9 g, yield: 92%) that is a mixture of cis and trans isomers. The oil is placed in a 1 L three-neck flask, taken up in DMSO (750 ml), and bubbled with oxygen while the solution is rapidly stirred. Aromatization is complete in 24–36 hours as determined by GC. The resulting solution is taken up in water (1 L) and washed with petroleum ether (3×750 ml). The combined organic layers are dried over anhydrous sodium sulfate and, upon removal of solvent, yield crystals of 3,6-ditrimethylsilyl-1,2-dihydrocyclobutabenzene (compound 4, 109.2 g, yield: 88% based on BCB).

3,6-Dibromo-1,2-Dihydrocyclobutabenzene (compound 5):

To a solution of compound 4 (100 g, 402 mmol) in methanol (2 L) is slowly added a solution of bromine (103.0 g, 625.8 mmol) in methanol (1 L). The addition takes place over 24 hours and the reaction is monitored by GC until complete (36 hours). The resulting solution is partitioned into water (1 L) and washed with petroleum ether (3×1 L). The combined organic layers are dried over anhydrous sodium sulfate. The solvent is removed to yield a yellow solid. The crude product is run through a short column of silica gel in petroleum ether:ethyl ether (90:10). Removal of eluent solvent yields white crystals of 3,6-dibromo-1,2-dihydrocyclobutabenzene (compound 5, 95 g, yield: 90%).

Dibutyl-1,2-Dihydrocyclobutabenzene-3,6-Carboxylate (compound 6)

A dry, magnetically stirred, 500 ml Schlenk flask is charged with compound 5 (40 g, 144 mmol), Pd(II) acetate (400 mg, 1.77 mmol), and triphenylphosphine (2.80 g, 10.6 mmol). The vessel is evacuated to 20 millitorr and refilled with carbon monoxide. This procedure is repeated four times. A solution of dry triethylamine (40 ml) and dry n-butanol (50 ml) is added via syringe. The resulting solution is degassed several times under rapid stirring to remove all gases dissolved in the solvents and the vessel is refilled with carbon monoxide. The contents of the vessel are then placed under a slight positive pressure with carbon monoxide and heated to 80° C. with very rapid stirring. The reaction requires about 48 hours and is monitored by GC until complete. The crude mixture is partitioned into water (1 L) and washed with petroleum ether (3×750 ml). The combined organic layers are dried over anhydrous sodium sulfate. The crude product is run through a short plug of silica gel with petroleum ether:ether (90:10) to remove catalyst. Removal of eluent solvent leaves a light yellow oil of dibutyl-1,2-dihydrocyclobutabenzene- 3,6-carboxylate (Compound 6, 40.60 g, yield: 95%)

1,2-Dihydrocyclobutabenzene-3,6-Carboxylic Acid (compound 7):

A solution of compound 6 (40 g, 142 mmol) and powdered sodium hydroxide (8 g, 200 mmol) is taken up in methanol (600 ml) with water (40 ml) and refluxed for two hours. Water (1 L) is added to dissolve excess sodium salts and the resulting solution is filtered. The mixture is then cooled to 0° C. and acidified to pH 7 to precipitate product. Filtration of the precipitated product and subsequent washing with acetone (300 ml) yields 1,2-dihydrocyclobutabenzene-3,6-carboxylic acid (XTA, compound 7, 26.5 g, yield: 97%) as a white powder.

In an alternative embodiment of the method (not shown on FIG. 1), compound 5 is converted to compound 7 by a Grignard reaction:

In a 300 ml round-bottom three-necked flask, fitted with a condenser, and equipped with a stirring bar, 0.950 g compound 5 and 2.00 g magnesium (Mg) are dried under reduced pressure. Dry ether (50 ml) is added to the flask under an inert ($N_2$) atmosphere. The reaction mixture is then heated to reflux. About 1 ml of dibromoethane is added to the reaction mixture to activate the surface of the Mg catalyst so that the reaction continues to reflux on its own. Additional dibromoethane (approximately 3.5 ml total in this example) is added as necessary to keep the reaction at reflux. The reaction progress is monitored by GC (the reactants have peaks at 2.45 and 5.44). When the product is the digrignard agent, $CO_2$ is bubbled through the reaction mixture. The reaction mixture is quenched with $H_2O$ (about 50 ml) and $H^+$ (concentrated HCl, about 5 ml). The product diacid is extracted from the aqueous solution with 50:50 THF and ethyl acetate. The organic solvents are evaporated under reduced pressure to yield a yellow solid. The yellow solid is dissolved in 6 N NaOH and filtered through a glass frit. The basic solution is re-acidified with concentrated HCl to precipitate purified crystals of compound 7. (0.5 g; 74% yield).

1,2-Dihydrocyclobutabenzene-3,6-Acid Chloride (compound 8)

To a dry, magnetically stirred, 1 L three-neck flask is added compound 7 (25.0 g, 130 mmol), benzyltriethylammonium chloride (65.0 mg, 0.29 mmol), and dry dichloromethane (600 ml). The mixture is brought to reflux and thionyl chloride (25.3 ml, 345 mmol) is added in one portion. The reaction requires about 24 hours and is monitored by GC until complete. The mixture is filtered hot and solvent is removed to yield dark yellow crystals which are sublimed (50 mtorr, 80° C.) to yield light yellow crystals. Recrystallization from dry ethyl ether yields white crystals of 1,2-dihydrocyclobutabenzene-3,6-acid chloride (compound 8, 28.6 g, yield: 96%).

Figure 2:
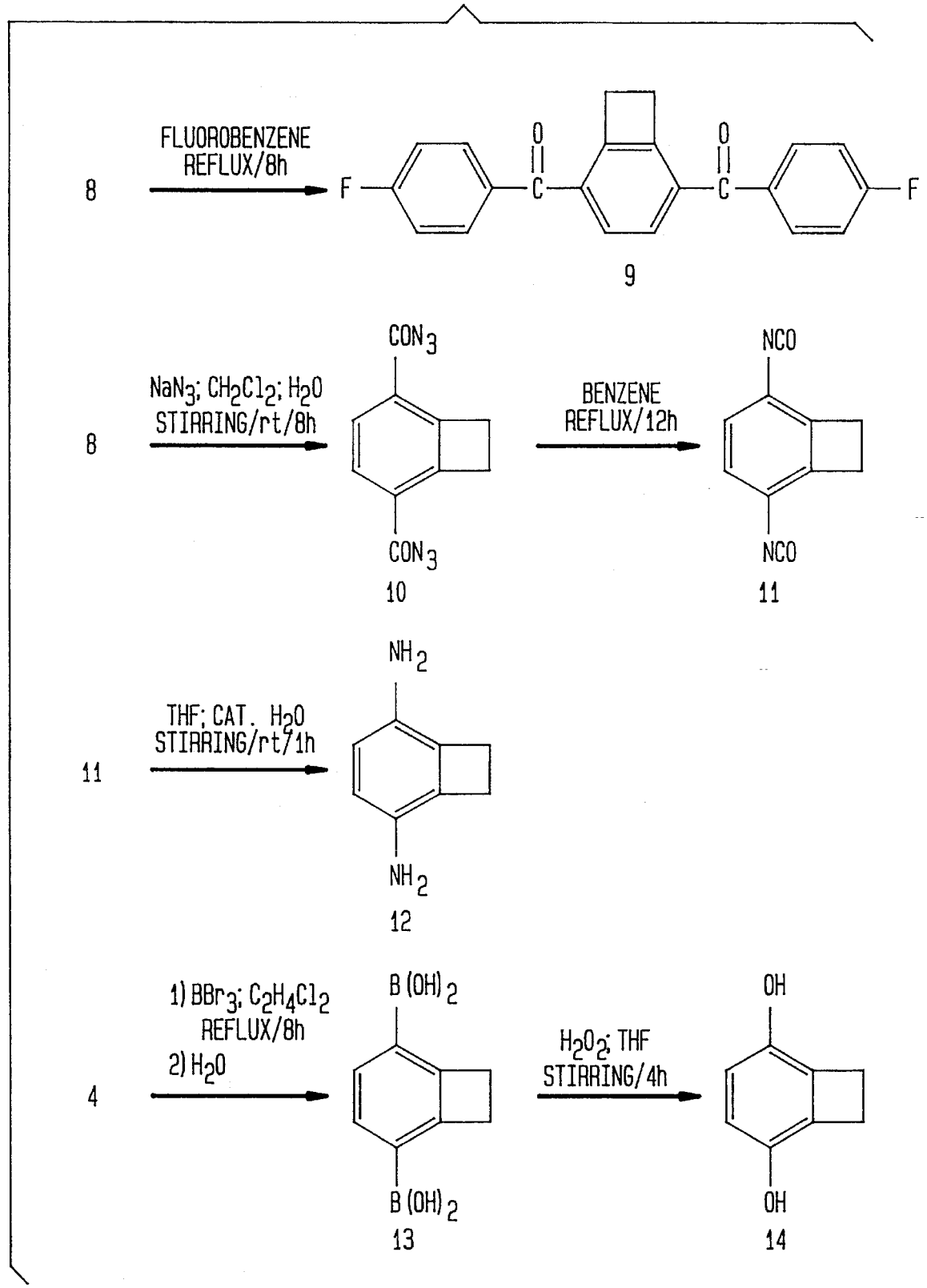
FIG. 2 and FIG. 3 show illustrative preparatory schemes for a series of cyclobutabenzene analogs within the contemplation of the present invention.
Figure 3:
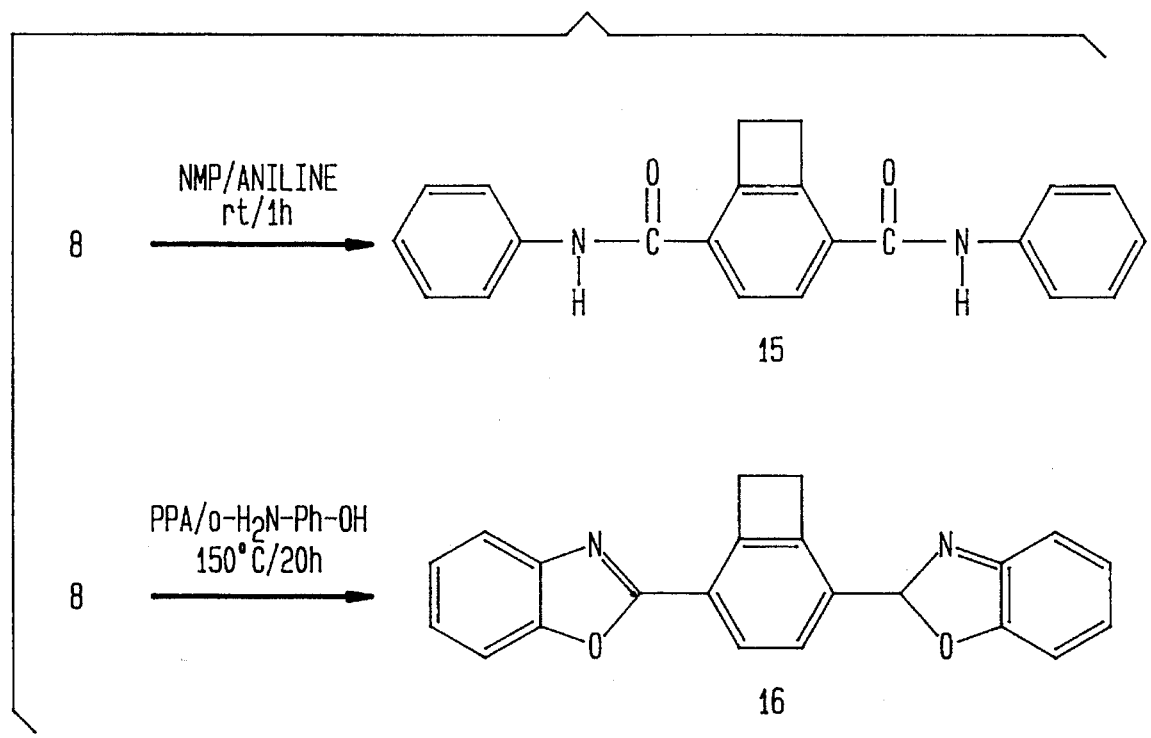

In additional illustrative embodiments of the invention, exemplary difunctionalized cyclobutabenzene analogs (compounds 9 through 16) have been synthesized in accordance with the reaction schemes illustrated in FIGS. 2 and 3.

3,6-(4-Fluorobenzoyl)-1,2-Dihydrocyclobutabenzene (compound 9)

Aluminum chloride (8.65 g, 65 mmol) is added to a solution of compound 8 (10.0 g, 44 mmol) in fluorobenzene (60 ml) in a three-neck, 250 ml flask fitted with a condenser, magnetic stirrer, and a nitrogen inlet. The mixture is refluxed for 12 hours and excess fluorobenzene is removed. The product is washed with 5% sodium hydroxide (100 ml), 5% HCl (100 ml), and water (1130 ml) to yield light yellow crystals. Two recrystallizations from acetone yields white crystals of 3,6-(4-fluorobenzoyl)-1,2-dihydrocyclobutabenzene (compound 9, 13.8 g, yield: 90%).

1,2-Dihydrocyclobutabenzene-3,6-Isocyanate (compound 11)

In a 500 ml round bottom flask, sodium azide (11.35 g, 175 mmol) is taken up in a suspension of water (200 ml) and dichloromethane (200 ml) under rapid stirring. Compound 8 (10.0 g, 44 mmol) is added in one portion. The reaction is monitored by GC until complete (4–6 hours). The resulting solution is extracted into water (100 ml) and washed with dichloromethane (3×150 ml). The combined organic layers are dried over anhydrous sodium sulfate and the solvent is removed to yield 1,2-dihydrocyclobutabenzene-3,6-acyl azide (compound 10, 9.7 g, yield: 92%) as white crystals. Compound 10 (9.0 g, 37 mmol) is taken up in dry benzene (250 ml) and refluxed under nitrogen for 12 hours The benzene is removed to yield light brown crystals. Recrystallization from dry ethyl ether yields white crystals of 1,2-dihydrocyclobutabenzene-3,6-isocyanate (compound 11, 6.4 g, yield: 93%).

1,2-Dihydrocyclobutabenzene-3,6-Diamine (compound 12)

A solution of compound 11 (6.0 g, 32 mmol) in dry THF (40 ml) is added dropwise to a solution of concentrated hydrochloric acid (20 ml) and THF (60 ml) over a period of 30 minutes with stirring. The reaction is allowed to proceed with stirring at room temperature for about an hour during which the amine-hydrochloride salt precipitates from solution. THF and excess HCl are removed under reduced pressure to yield white crystals of 1,2-dihydrocyclobutabenzene- 3,6-diamine (compound 12, 6.4 g, yield: 93%) as the hydrochloride salt.

3,6-Hydroxy-1,2-Dihydrocyclobutabenzene (compound 14)

In a three-neck, 250 ml flask fitted with a condenser, magnetic stirrer, and a nitrogen inlet, boron tribromide (15.0 g, 60 mmol) is added to a solution of compound 4 (5.0 g, 20 mmol) in dry dichloroethane (150 ml). The reaction mixture is brought to reflux and requires about 12 hours for completion. The mixture is taken up in water (300 ml) and washed with ethyl acetate (3×200 ml). The combined organic layers are dried over anhydrous sodium sulfate. Removal of solvent yields a brown solid which is taken up in 6N sodium hydroxide (100 ml) and filtered to remove organic impurities. Acidification of the filtrate to pH 7 and filtration of the resulting precipitate yields 1,2-dihydrocyclobutabenzene-3, 6-boronic acid (compound 13, 3.2 g, yield: 83%) as a white powder.

Compound 13 (1.0 g, 5 mmol) is added to a solution of diethyl ether (100 ml) and 30% hydrogen peroxide under rapid stirring at room temperature. The reaction is complete in 4 hours. Excess peroxide is quenched with 10% ferrous ammonium sulfate. The solution is brought to pH 7 and extracted with diethyl ether (3×100 ml). The combined organic layers are dried over anhydrous sodium sulfate. Removal of solvent yields 3,6-hydroxy-1,2dihydrocyclobutabenzene (compound 14, 1.47 g, yield: 65%) as a yellow oil.

1,2-Dihydrocyclobutabenzene-3,6-Benzamide (compound 15)

A 100 ml, magnetically stirred, round bottom flask is charged with aniline (1.63 g, 17.2 mmol) and N-methyl-1-pyrrolidinone (5 ml). Compound 8 (1.0 g, 4.4 mmol) is added with stirring. A yellow solution results. The reaction is complete within about one hour. The solution is filtered to produce yellow crystals which are washed with water (50 ml) and acetone (50 ml) to yield white crystals of 1,2-dihydrocyclobutabenzene-3,6-benzamide (compound 15, 1.45 g, yield: 97%).

1,2-Dihydrocyclobutabenzene-3,6-Benzoxazole (compound 16)

A 250 ml-three neck flask equipped with a mechanical stirrer and a nitrogen inlet is charged with compound 8 (1.0 g, 4.4 mmol), degassed polyphosphoric acid (50 ml), and 2aminophenol (1.9 g, 17.4 mmol). The reaction mixture is heated to 90° C. with stirring and degassed to remove HCl. The reaction mixture is then heated to 150° C. for 20 hr. The resulting solution is partitioned into water (500 ml), brought to neutral pH conditions via addition of sodium hydroxide solution, and filtered to collect the solid. Recrystallization of the solid material from dimethyl sulfoxide yields fluffy, pale yellow crystals of 1,2-dihydrocyclobutabenzene- 3,6-benzoxazole (compound 16, 1.19 g, yield: 80%).

To explore the thermal behavior of the two model XTA compounds related to the known high-performance polymers PPTA (compound 15) and PZBO (compound 16), differential scanning calorimetry (DSC) experiments were conducted. The results are reported on Table 1 and reveal a reversible melting followed by an irreversible chemical reaction. This reaction, presumably the opening of the cyclobutane ring, proceeds appreciably above 300° C. Both compounds are stable under the synthesis and processing conditions described hereinabove.

TABLE 1

| DSC data of 1,2-Dihydrocyclobutabenzene Model Compounds 15 and 16 | | | |
|---|---|---|---|
| Compound | Molecular Formula | $T_m^a$ | $T_r^b$ |
| 15 | $C_{21}H_{18}N_2O_2$ (330.1) | 314° C. | 335° C. |
| 16 | $C_{22}H_{14}N_2O_2$ (338.4) | 303° C. | 349° C. |

Figure 4:
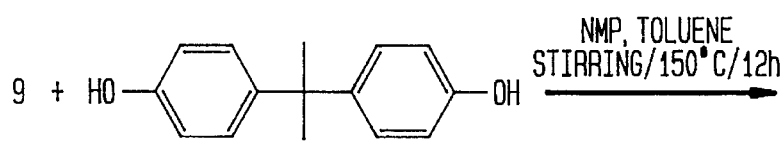
FIG. 4 shows illustrative preparatory schemes for two resins prepared with the difunctionalized cyclobutabenzene monomers of the present invention, in particular, a poly(paraphenylene diamine terephthalate) and a poly(ether ether ketone ketone)
Figure 4:
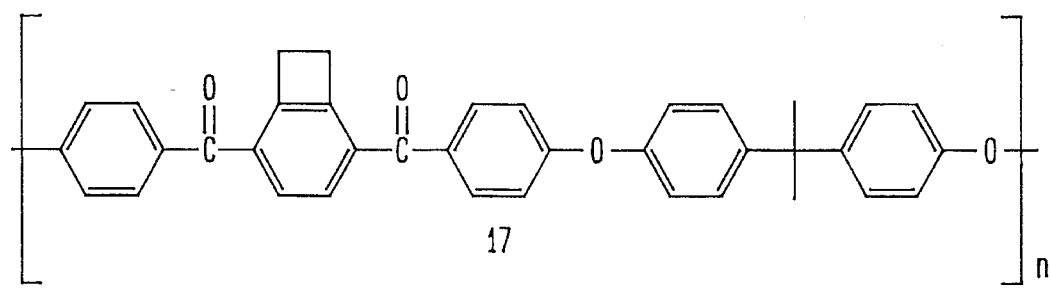
Figure 4:
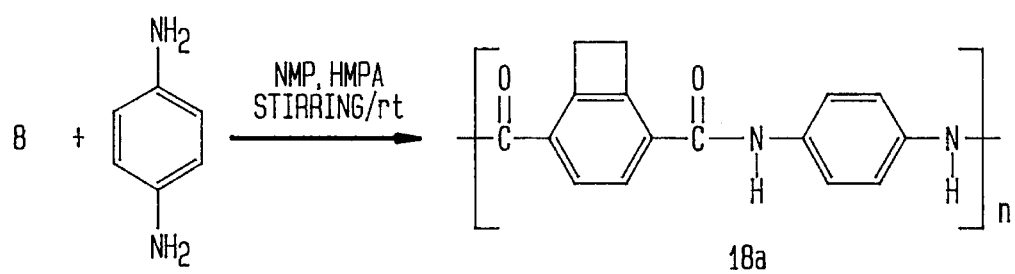
Figure 4:
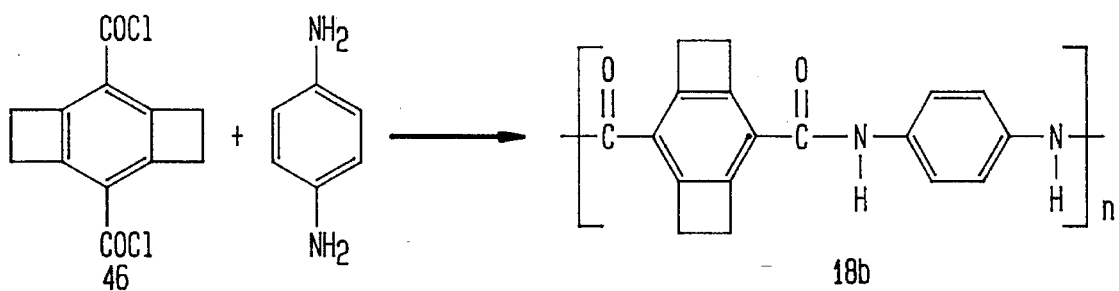

$^aT_m$ — reversible melting transition (heating rate = 20° C./min)
$^bT_m$ — onset of irreversible chemical reaction In a further specific embodiments of the invention, resins have been formed by polymerization of the cyclobutabenzene monomers of the present invention with copolymers which are capable of reacting with the X/Y-functionalities of the cyclobutabenzene monomer. FIG. 4 shows illustrative preparatory schemes for two such illustrative resins.

Poly(Ether Ether Ketone Ketone) (compound 17, PEEKK-BCB)

To a flask equipped with a magnetic stirrer, a Dean-Stark trap, and a nitrogen inlet is added compound 9 (2.0901 g, 6 mmol), 4,4'-isopropylidenediphenol (1.37 g, 6 mmol), dry potassium carbonate (1.74 g, 12.6 mmol), dry N-methyl-1-pyrrolidinone (NMP, 16 ml), and dry toluene (12 ml). The reaction mixture is heated to 140° C. with stirring for 3 hours to dehydrate the reaction and remove the toluene. After removal of toluene, the reaction is stirred for another 3 hours at 140° C. The mixture is then precipitated into water and the polymer is washed with acetone and dried at 60° C. under vacuum for 24 hours to yield the poly(ether ether ketone ketone), compound 17 (3.16 g, yield: 98% ).

Comparative DSC studies were conducted with poly-(ether ether ketone ketone) polymers to determine the effect of crosslinking. Poly(ether ether ketone ketone) polymers were synthesized without the BCB function and with the BCB function (compound 17).

Referring to Table 2, the PEEKK without BCB showed a reversible melt at 155° C. and decomposed at 405° C. (Run #1). PEEKK-BCB exhibited a similar melt at 158° C., but also an irreversible reaction at 305° C. The heating was stopped at 350° C and cooled to 50° C. to avoid decomposition (Run #2). The same PEEKK-BCB sample was again heated and no melt or reaction was observed until decomposition at 410° C. (Run #3). Table 2 shows that decomposition temperature is not greatly increased by adding the BCB functionality. However, once crosslinked, PEEKK-BCB does not melt. This characteristic extends its mechanical usefulness safely to about 350° C. In contrast, PEEKK without the BCB functionality melts at 150° C., thereby losing its mechanical usefulness at a much lower temperature.

TABLE 2

| DSC data of PEEKK polymers | | | | |
|---|---|---|---|---|
| Compound | Run # | $T_m^a$ | $T_r^b$ | $T_d^c$ |
| PEEKK | 1 | 150° C. | — | 405° C. |
| PEEKK-BCB | 2 | 158° C. | 305° C. | — |
|  | 3 | — | — | 410° C. |

$^aT_m$ — reversible melting transition (heating rate = 20° C./min)
$^bT_r$ — onset of irreversible chemical reaction
$^cT_d$ — onset of irreversible chemcial decomposition

Poly(paraphenyl Diamine Terephthalate) Copolymerized With XTA (compound 18, PPTA-co-XTA)

XTA is incorporated into the backbone of a polyamide related to poly(paraphenylene diamine terephthalate). The resulting polymer is herein designated PPTA-co-XTA.

To a flask equipped with a magnetic stirrer and a nitrogen inlet is added para-phenylene diamine (1.0814 g, 10 mmol), N-methyl-1-pyrrolidinone (NMP, 13.4 ml), and hexamethylphosphoramide (HMPA, 26.8 ml). At room temperature, under very rapid stirring, compound 8 (2.2906 g, 10 mmol) is added in one portion. The reaction mixture is rapidly stirred for 15 minutes and then allowed to stand for 10 hours. The polymer is precipitated in 2N sodium hydroxide, washed with acetone, and dried under vacuum overnight to yield the PPTA-co-XTA compound 18 (2.5 g, yield: 95%).

This procedure was repeated using varying molar ratios of TA:XTA in the polymerization reaction to show the ability of XTA to be used as a comonomer with TA in polymer synthesis. The ratio of TA:XTA and the subsequent intrinsic viscosities of the resulting PPTA-based polymer are shown in Table 3. Table 3 reports the intrinsic viscosity (in dL/g) of the polymer in 100% sulfuric acid as measured in an Ubbelodhe capillary tube at 30° C. Table 3 demonstrates that XTA can be incorporated successfully into current polymer synthesis techniques to yield a high molecular weight polymer.

TABLE 3

Molar ratio and intrinsic viscosity of copolymers based on PPTA

| mmol diamine | mmol TA | mmol XTA | intrinsic viscosity |
| --- | --- | --- | --- |
| 10 | 0 | 10 | 5.7 |
| 10 | 5.0 | 5.0 | 6.6 |
| 10 | 7.5 | 2.5 | 4.9 |
| 10 | 9.0 | 1.0 | 5.3 |
| 10 | 9.5 | 0.5 | 5.8 |
| 10 | 10 | 0 | 5.5 |

Figure 5:
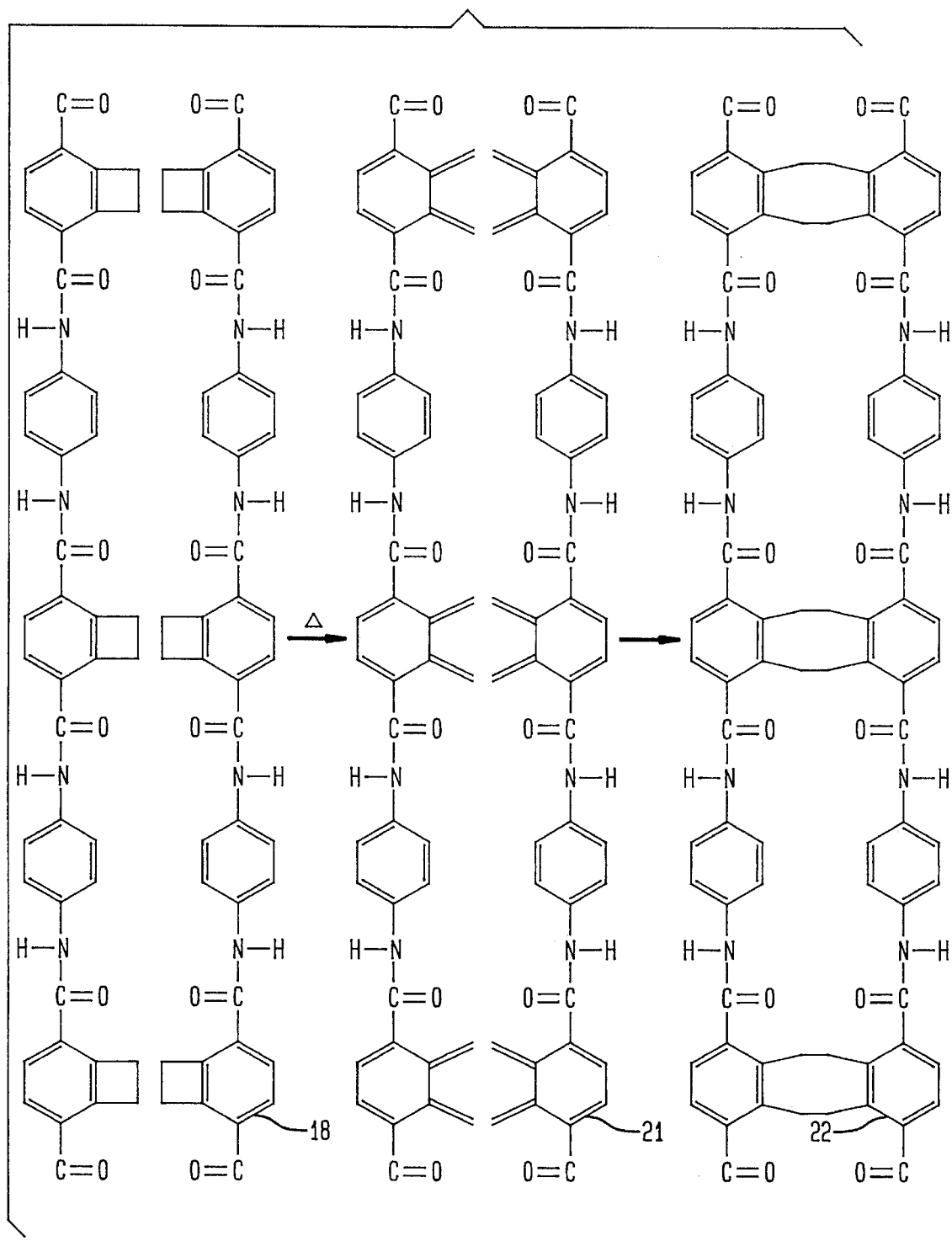
FIG. 5 is molecular structure depiction of a resin having cyclobutabenzene incorporated into a polymer backbone of the type comprising a polyamide, specifically a poly(paraphenylene diamine terephthalate), and the consequent structure of the improved polymer after crosslinking through the cyclobutane functionalities.

Referring to FIG. 5, the BCB-containing polymer, compound 18, can be chemically crosslinked by subjecting the resin to a temperature in excess of 300° C. to open the cyclobutane ring to form the highly reactive intermediate (o-quinodimethane) 21 which reacts with other open rings to form a highly crosslinked three-dimensional polymer network 22.

Incorporating the cyclobutabenzene functionality into the polymer backbone has unique advantages over the prior art polymerization techniques. First, the BCB monomers of the present invention can be incorporated into the polymer backbone in any amount that is required to achieve a desired property. Second, crosslinking is rapid and can be performed before, during, or after fiber spinning or casting of films. This eliminates the problem of disrupting crystallinity. Crosslinking can be easily achieved by heating the product to a temperature in excess of 300° C. and no catalysts are required for initiation. Furthermore, no volatile by-products are released during the crosslinking reaction, which is accompanied by a minimal change in volume. These advantageous characteristics enable the high orientation and order that exists in the known high-performance polymers to be retained.

Figure 6:
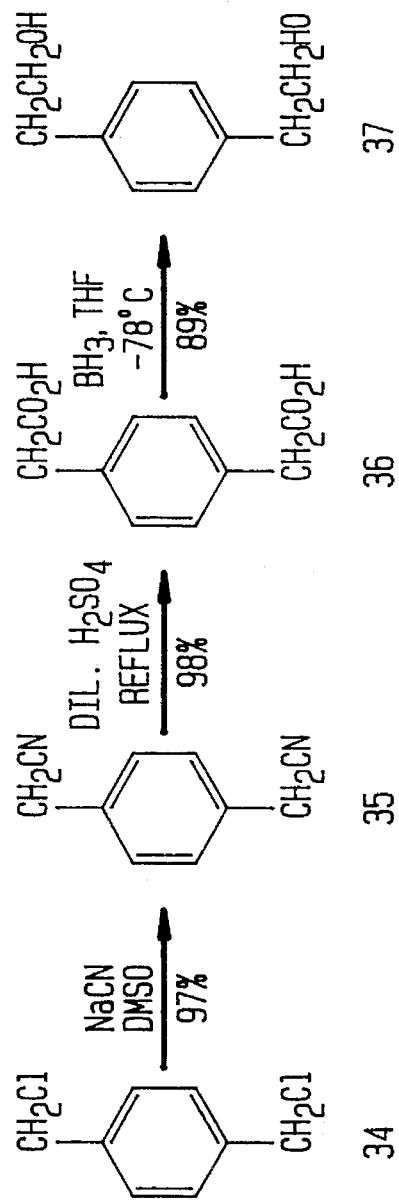
FIG. 6 is an illustrative preparatory scheme for dicyclobutabenzene.
Figure 6:
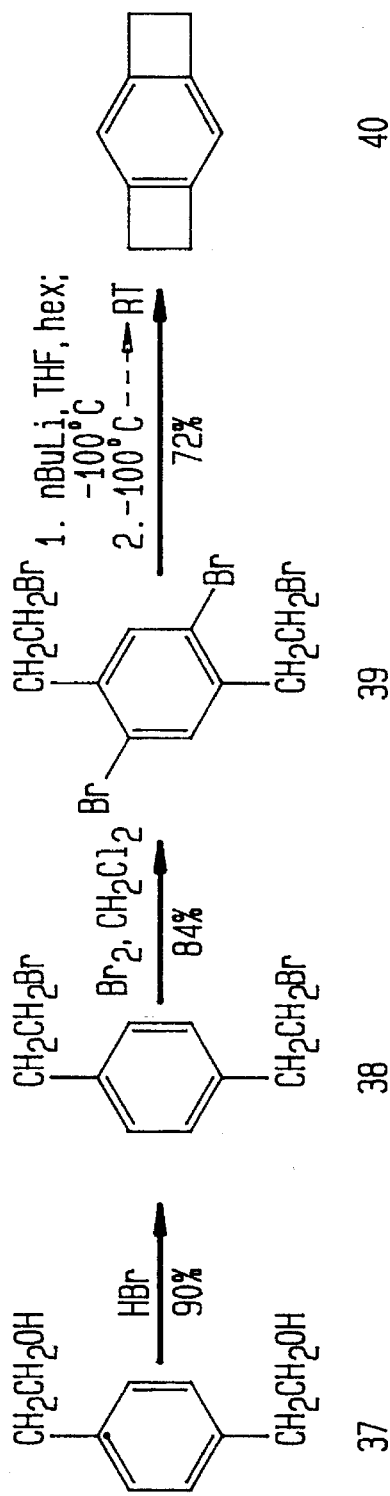

In another method embodiment of the invention, benzodicyclobutabenzene can be prepared in accordance with the illustrative preparatory scheme of FIG. 6. It is to be clearly understood, however, that the preparatory schemes included in the present application, are intended to demonstrate a successful method of practicing the invention, and in no way are intended to limit the scope of the invention. For example, benzodicyclobutabenzene may also be made by flash vacuum pyrolysis of 2,5-bis(chloromethyl)-p-xylene or 4,6-bis(chloromethyl)-m-xylene. In the method illustrated in FIG. 6, for example, benzodicyclobutanbenzene (compound 40) can be synthesized from commercially available phenylene diacetic acid (compound 36, FIG. 6) or from the inexpensive, and commercially available dichloride, $\alpha,\alpha'$-dichloro-p-xylene (compound 34)

Referring to the preparatory scheme of FIG. 6, the dichloride compound 34 is converted to the diacetonitrile (compound 35). The diacetonitrile is converted to the diacid (compound 36) in dilute sulfuric acid. The diacid is reduced to the corresponding dialcohol (compound 37). The dialcohol is converted to the hydrocarbon, benzodicyclobutabenzene (compound 40), through a series of halogenated intermediates. In the particular embodiment shown in FIG. 6, a dibromide, 1,4-bis(1-bromoethyl)benzene (compound 38), is formed by subjecting the dialcohol to hydrogen bromide (HBr). The dibromide is isolated and purified prior to selective dibromination to yield the tetrabromide (compound 39). Compound 39 is the precursor in a low-temperature double Parham cyclization resulting in the dicyclobutabenzene compound 40 [Brewer, et al., Tet. Lett., Vol. 52, pp. 4573–4574 (1995); Parham, et al., J, Org. Chem., Vol. 41, pp. 1184–1186 (1976); Bradsher, et al., J. Org. Chem., Vol. 46, pp. 4608–4610 (1981)]

Figure 7:
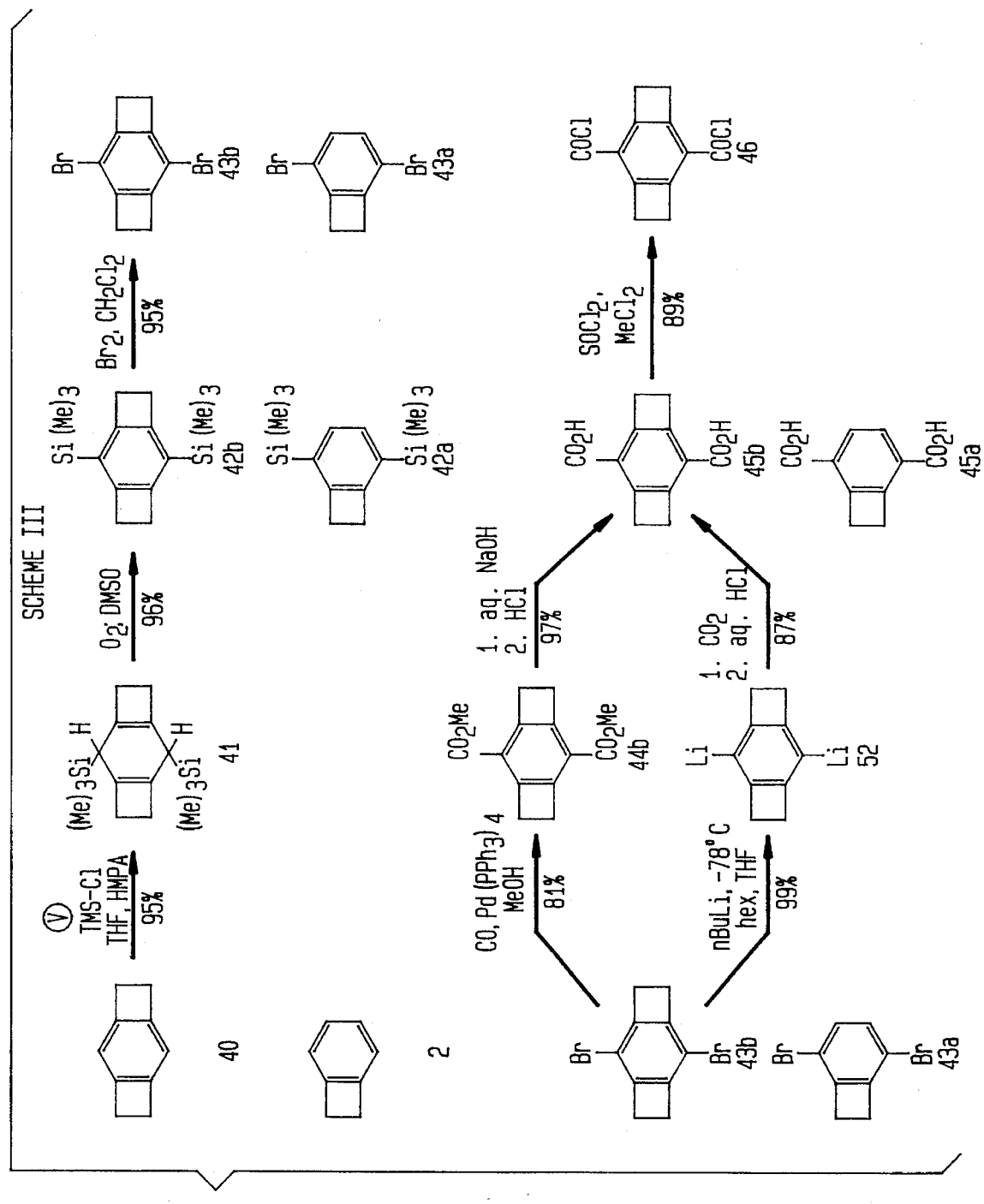
FIG. 7 is an illustrative preparatory scheme for producing XTA, DXTA, and their reactive acid or diacid halide analogs.

In order to produce reactive difunctionalized dicyclobutabenzene monomers, the hydrocarbon compound 40 is reduced to a diene, 1,4-bis(trimethylsilyl)diene (compound 41), as shown on FIG. 7. FIG. 7 is an illustrative preparatory scheme for producing DXTA (compound 45), and its diacid halide equivalent (compound 46). Of course, the methods portrayed on FIG. 7, as well as those on FIG. 11, may be applied to the hydrocarbon BCB (compound 2, FIG. 1 ) as well as hydrocarbon DBCB (compound 40). In the figures, the corresponding intermediates and products are labelled "a" and "b," respectively, for BCB and DBCB as the starting hydrocarbon.

FIG. 7 includes a technique of preparative electrochemical reductive silylation wherein the source of reducing electrons for the reaction comes from the oxidation of a sacrificial material at an electrochemical anode. The sacrificial material used in the embodiment described herein is aluminum, however, other metals and alloys of low oxidation potential may be used in accordance with the principles of the invention.

The diene, compound 41, is aromaticized with oxygen at room temperature to yield the 3,6-trimethylsilyl benzocyclobutene intermediate compound 42a, or its dicyclobutabenzene analog, compound 42b. Bromodesilylation results in the corresponding dibromides (43a,b). Compound 43b, for example, is converted to the corresponding 3,6-diester (compound 44b) with palladium-catalyzed carbonylation. Palladium-catalyzed carbonylation requires long reaction times for reaction scales of greater than 0.5 mole. For larger scale reactions, the use of a stainless steel bomb at CO pressures of ca. 100 psi improves conversion time. In an alternative embodiment, preferred for up to 20 mmol scale, diacid (compounds 45a,b or XTA and DXTA, respectively) is produced by low temperature lithiation of the dibromide compounds 43a,b, followed by quenching in $CO_2$. Hydrolysis of the diester (e.g., compound 44b) with aqueous base at reflux, followed by acid workup, produces the diacid compounds 45a,b. The diacid compounds 45a,b are converted to the corresponding diacid halide compounds 46a,b using thionyl chloride as described hereinabove.

The preparatory schemes of FIGS. 6 to 7 are described in greater detail below:

1,4-bis(Cyanomethyl)benzene (compound 35)

Starting with 2,5-bis(chloromethyl)-p-xylene (compound 34, available form Aldrich Chemical Company, Milwaukee, Wis.), a procedure described by Friedman and Shecter, J. Org. Chem., Vol. 25, pp. 877–879 (1960) using NaCN in DMSO at 0° C. results in compound 35, 1,4-bis(cyanomethyl)benzene (mp 95° C.).

1,4-Phenylenedicarboxylic acid (compound 36)

A 250 ml flask is charged with 10 g (64 mmol) of compound 5, 50 ml water, and 25 ml concentrated HCl. The mixture is brought to reflux, with stirring, and monitored by gas chromatrography to completion. When the starting material is consumed, the suspension is cooled on ice, filtered, washed with water, and dried under vacuum to yield 8.95 g (72% yield) of a white solid, 1,4-phenylenedicarboxylic acid (mp 149°–150° C.).

1,4-bis(2-Hydroxyethyl)benzene (compound 37)

The diacid compound 36 (20g) is placed in a dry 500 ml sidearm flask equipped with a reflux condenser, septum inlet, and magnetic stirrer. The contents are evacuated and purged with dry nitrogen several times. Dry THF is added (25 ml) and the mixture is brought to 0° C. A solution of borane-THF complex (266 ml of 1.0M soln.) is added dropwise to the solution. The solution is stirred at 0° C. for 4 hours, followed by 6 hours at 20° C. Workup with a 1:1 THF-water mixture (70 ml) and the addition of 40 g potassium carbonate saturates the aqueous phase and allows easy separation of the THF-alcohol phase. The combined THF extracts are dried over magnesium sulfate ($MgSO_4$) and concentrated under vacuum to afford a solid white product, 1,4-bis(2-hydroxyethyl)benzene in 89.4% yield (15.3 g; mp 83°–84° C.).

1,4-bis(2-Bromoethyl)benzene (compound 38)

A suspension of 1,4-bis(2-hydroxyethyl)benzene (1.77 g; 10.7 mMol) in 25 ml of 48% hydrobromic acid is refluxed and stirred for 5 hours. The mixture is extracted with dichloromethane, and the extracts are dried, filtered, and concentrated under vacuum to yield a brown solid. Recrystallization from hexane afforded 2.8 g of the dihalide, 1,4-bis(2-bromoethyl)benzene, as pale yellow needles (90% yield; mp 71°–72° C.); $^1$H NMR (300 MHZ, $CDCl_3$): δ7.15 (s, 4H); 3.54 (t, 4H); 3.13 (t,4H).

2,5-Dibromo-1,4-bis(2-bromoethyl)benzene (compound 39)

Compound 38 (1.28 g; 4.4 mMol) is dissolved in 28 ml of dichloromethane. Iron filings (0.06 g) and iodine (0.02 g) is added to the solution, followed by the dropwise addition of bromine (1.53 g; 9.6 mMol). The mixture is stirred at room temperature for 2 days, then filtered, washed with 15% sodium thiosulfate solution, dried, and concentrated under reduced pressure. The resulting brown solid is sublimed to give a white solid. Subsequent recrystallization from hexane yielded colorless needles of 2,5-dibromo-1,4-bis(2-bromoethyl)benzene in 84% yield (1.67 g, mp 106°–108° C. $^1$H NMR (300 MHZ, $CDCl_3$): δ7.44 (s,2H); 3.55 (t,4H); 3.22 (t,4H).

Benzo[1,2:4,5]dicyclobutene (compound 40)

The hydrocarbon benzo[1,2:4,5]dicyclobutene, also known as benzodicyclobutabenzene, is obtained from 2,5-dibromo-1,4-bis(2-bromoethyl)benzene (compound 39) by a dual Parham cyclization procedure (Bradsher, et. al., J. Org, Chem., Vol 46, pp. 4608–4610 (1981). The product was recrystallized from methanol to give colorless plates (yield 72%); mp 100° –101° C.

$^1$H NMR (300 MHZ, $CDCl_3$): δ6.78 (s, 2H); 3.12 (s, 8H).

1,4-bis(Trimethylsilyl)benzo[1,2:4,5]dicyclobutene (compound 42b)

A specially modified two-piece airtight chamber designed to hold a solid aluminum rod (anode), a stir bar, an electrical lead to the cathode (glassy carbon cloth), and a nitrogen/vacuum inlet is charged with 527 mg of hydrocarbon compound 40 (5.0 mMol), 1 ml of dry THF, 0.10 g LiCl, 2 g hexamethylphosphoramide (HMPA), and finally 7 ml of chlorotrimethylsilane (6.0 g, 55 mMol).

A glassy carbon cloth cathode is formed into a cylindrical shape, placed into the bottom of the flask, and clipped to the interior end of a copper cathode lead. The copper cathode lead is sealed into (passing through) a glass stopper inserted into a ground glass joint coming from the side of the vessel top. The exterior end of this copper lead in turn is clipped to the negative lead of a D.C. power supply. The flask top is replaced with an o-ring seal and clamped, and the aluminum rod anode is positioned directly through the joint at the top through the center of the flask, reaching the level of the stir bar. The positive lead is attached to the top of this rod outside the flask. The rod passes through a threaded-glass stopper with a securing o-ring that is tightened down using a Teflon screw plug. The entire setup is designed to allow attachment to a vacuum manifold for degassing and purging with inert gas. Once the vessel is closed, degassing and back-filling with argon or nitrogen is performed several times. The final degassing procedure is preceded by turning on the power supply. Initial current is consumed by formation of aluminum hydroxide and concurrent hydrogen gas formation. Complete removal of HCl gas is the final step in eliminating any trace amounts of water present in the mixture. The D.C. voltage is set to 4.0 V D.C. The resulting current varies between about 200–800 mA. The reaction is monitored to completion by GC, the current is monitored until dropping near zero (about 1–2 days).

The entire contents are poured onto ice and the organic fraction is separated using hexane, dried over $MgSO_4$, and concentrated to yield 1.05 g (94.6%) of unaromaticized oil product (compound 39). Compound 39 is taken up in DMSO (20 ml) with vigorous stirring action in a sealed 3-neck flask equipped with a submerged glass frit oxygen outlet tube. The material is stirred under oxygen atmosphere for a period of 5–6 hours until the product has fully aromaticized as evidenced by GC analysis. This mixture is diluted with cold water, extracted into pentane, dried, and concentrated to a white solid. Recrystallization from methanol affords pure white crystals of 1,4-bis(trimethylsilyl)benzo[1,2: 4,5]dicyclobutene, compound 42b; 94.6% isolated yield, mp 148°–149° C. $^1$H-NMR (200 MHZ, $CDCl_3$): δ3.13 (s,8H), 0.25 (s, 18H).

3,6-Dibromobenzo[1,2:4,5]dicyclobutene (compound 43b)

The carbon-silicon bond of compound 42b is cleaved by electrophilic substitution [see, Eaborn, et at., I. Chem. Soc., Perkin I, pp. 2481–2484 (1972)]. Compound 42b (0.850 g; 3.1 mMol) is added to a clean round-bottomed flask equipped with an addition funnel. A 50% solution of dichloromethane in methanol is added to the flask and stirred to fully dissolve the starting material. Bromine (4.95 g, 1.6 ml, 10 eq.), dissolved in the same solvent mixture, is slowly added dropwise at room temperature. The mixture is monitored by GC, and when the starting material and monosubstituted product were no longer visible, the contents were combined with 10% NaOH solution and extracted into ether. Combined extracts were dried over $MgSO_4$ and concentrated on a vacuum line to afford 0.85 g of 95% pure off-white crystals of 3,6-dibromobenzo[1,2:4,5]dicyclobutene (compound 43b) in 95% yield. Recrystallization from hexane affords white needles. $^1$H NMR (300 MHZ, $CDCl_3$): δ3.00 (s, 8H).

Dimethyl-1,2,4,5-dicyclobutabenzene-3,6-carboxylate (compound 44b)

A sealed bomb reaction converts 3,6-dibromobenzo[1,2:4,5]dicyclobutene (compound 43b) to the corresponding ester. Typically, compound 43 (300 g; 1.15 mol.) is dissolved completely in the warm methanol (1.0 L) along with palladium (II) chloride or acetate in catalytic amounts (0.1 mol. %). Then the bomb is sealed and placed under positive CO pressure at about 100 psi. The mixture is magnetically stirred in an oil bath at 80° C. and monitored to completion by GC. Isolated yield of dimethyl-1,2,4,5-dicyclobutabenzene-3,6-carboxylate for this procedure is 80.8%; $^1$H-NMR (300 MHZ, $CDCl_3$): δ3.85 (s, 6H), 3.31 (s,8H).

3,6-Benzo[1,2:4,5]dicyclobutenedicarboxylic acid (DXTA, compound 45)

A dry sidearm flask is charged with 100 mg of compound 52 (0.35 mMol) in 3.5 ml of dry THF. The mixture is stirred and cooled to −78° C. n-Butyl lithium (0.76 mMol, 2.2 eq.) is added slowly to maintain the temperature below −75° C. The reaction is monitored by GC until bromine-lithium exchange is complete. Dry $CO_2$ is passed through a column of oven-dried $CaCl_2$ and into the reaction mixture under about 10 psi for several hours. Then the mixture is warmed to room temperature before being combined with 10 ml 2N HCl solution. This suspension is brought to a pH of 9, washed with hexane, and re-acidified to precipitate 3,6-benzo[1,2:4,5]dicyclobutenedicarboxylic acid as a white solid, collected by filtration (60 mg; yield 79.3%). $^1$H NMR (300 MHZ, DMSO-d6): δ3.37 (s,8H).

3,6-Benzo[1,2:4,5]dicyclobutenedicarboxylic acid dichloride (compound 46)

In a dry flask:80 mg of compound 45 (0.37 mMol) is dispersed in 30 ml dry dichloromethane with magnetic stirring. To this is added 0.1 ml (0.163 g, 1.37 mMol) thionyl chloride, and $BnEt_3NCl$ (5 mg, 0.02 mMol). The mixture is heated to reflux for 2 hours and monitored by GC. The mixture is filtered hot and the solvent is removed to yield yellow crystals. Sublimation of the yellow crystals, followed by recrystallization from ether, yielded white crystals of 3,6-benzo[1,2:4,5]dicyclobutenedicarboxylic acid dichloride (88 mg, 94% yield). $^1$H NMR (300 MHZ, $CDCl_3$):δ3.43 (s, 8H).

In specific examples of resins made from the monomers of the present invention, the homopolymer PPDXTA (compound 18b, FIG. 4) was prepared by standard condensation polymerization of DXTA-diacid chloride (compound 46) and p-phenylene diamine. More specifically, the condensation reaction was a low temperature solution polymerization in NMP:HMPA solvent at 0° C. The resulting PPDXTA homopolymer had a molecular weight of from about 18,000 to 20,000.

Figure 8:
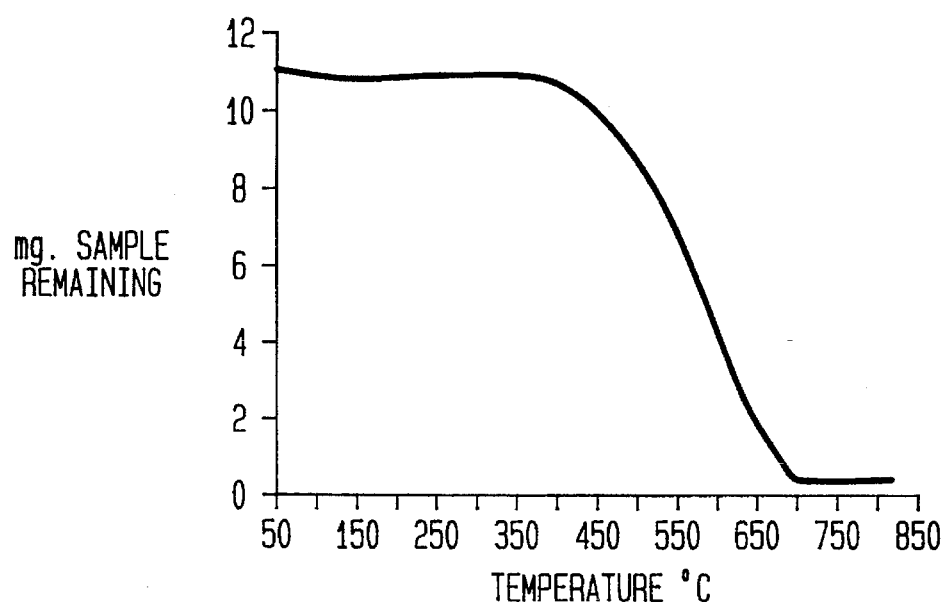
FIG. 8 is a thermogravimetric analysis plot for the homopolymer.
Figure 9:
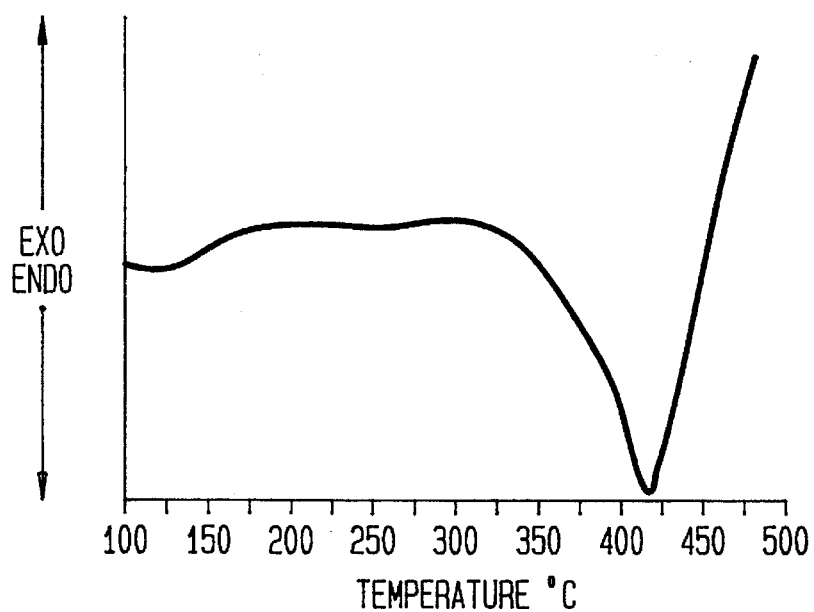
FIG. 9 is a representative differential scanning calorimetry trace of PPDXTA.

FIG. 8 is a thermogravimetric analysis plot for the homopolymer PPDXTA. Referring to FIG. 8, the onset of thermal degradation is visible at approximately 380° C. which is greater than the temperature required to institute crosslinking (about 250° C.) in a DXTA-containing polymer. FIG. 9 is a representative differential scanning calorimetry trace of PPDXTA which shows that the exotherm maxima for PPDXTA occurs at 420° C., which is significantly higher than the exotherm of the homopolymer PPXTA.

Figure 10:
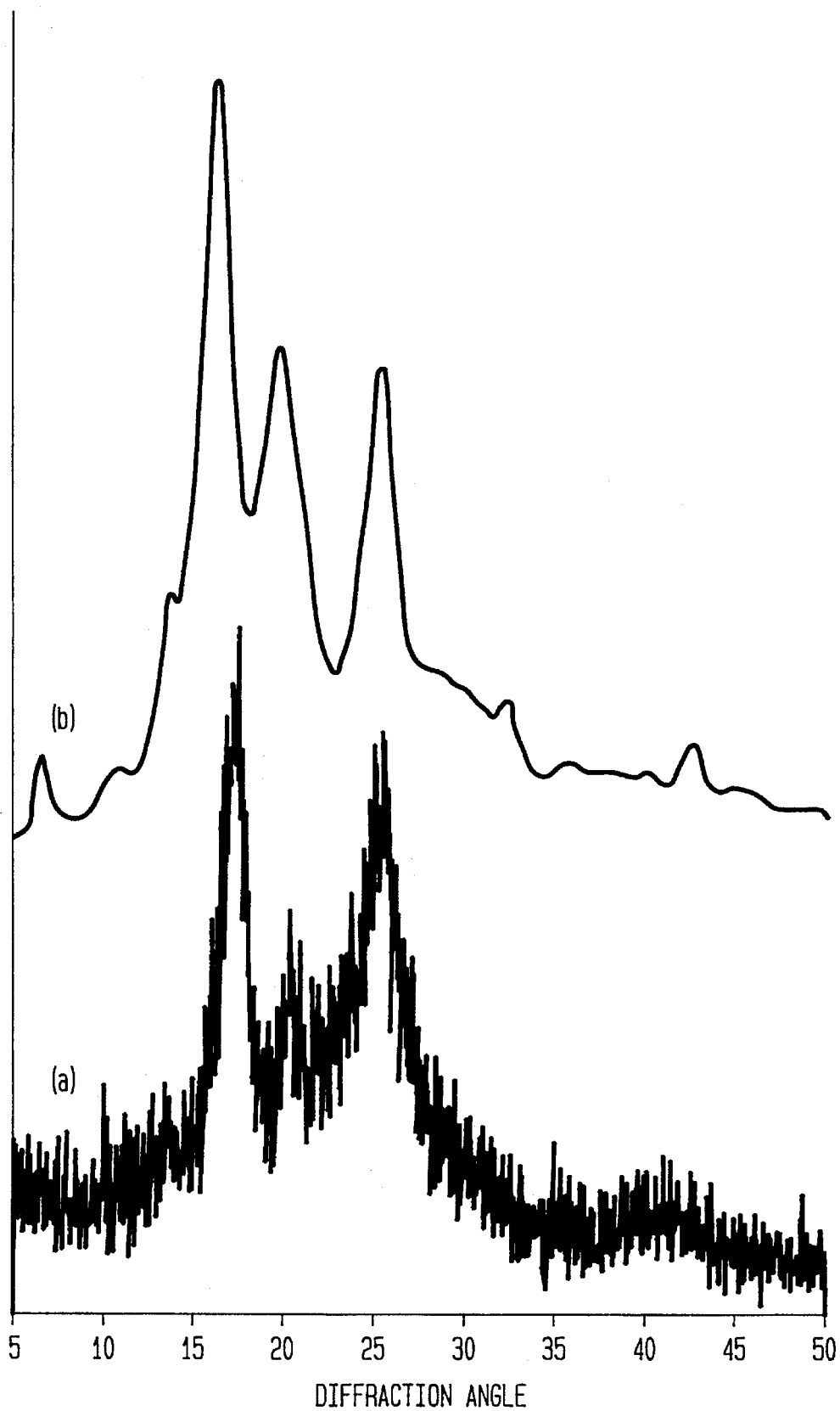
FIG. 10 is a plot of x-ray diffraction data for PPTA, PPXTA, and PPDXTA.

Wide angle x-ray diffraction was performed on PPDXTA powder using a symmetric theta-theta diffractometer and Cu Kα radiation (λ=1.54Å). The results are shown in FIG. 10 which is a plot of x-ray diffraction data for PPDXTA (a) as compared to simulated data (b) for the crystal structure of DXTA. Referring to FIG. 10, two diffraction peaks can be distinguished clearly for PPDXTA. The diffraction peaks correspond to d-spacings of 7.8Å and 3.5Å, respectively. The diffraction pattern is remarkably different from those resulting from x-ray diffraction studies of PPTA or PPTA-co-XTA copolymer. The position and sharpness of the 7.8Å peak suggests a distinctive crystallinity in the solid-state polymer. In additional studies, data was generated using heat-treated (420° C.) PPDXTA. The pattern for the heat-treated PPDXTA exhibited little difference from the as-synthesized PPDXTA shown in FIG. 10. There was a slight shift of the peak and an increase of the crystallite size as set forth in Table 4 hereinbelow.

TABLE 4

| COMPARISON OF PPDXTA DIFFRACTION PEAKS BEFORE AND AFTER HEAT TREATMENT | | | | |
|---|---|---|---|---|
| | as-synthesized | | heat-treated | |
| | d-spacing (Å) | crystallite size (Å) | d-spacing (Å) | crystallite size (Å) |
| peak I | 7.8 | 33 | 7.5 | 40 |
| peak II | 3.5 | 35 | 3.5 | 35 |

Figure 11:
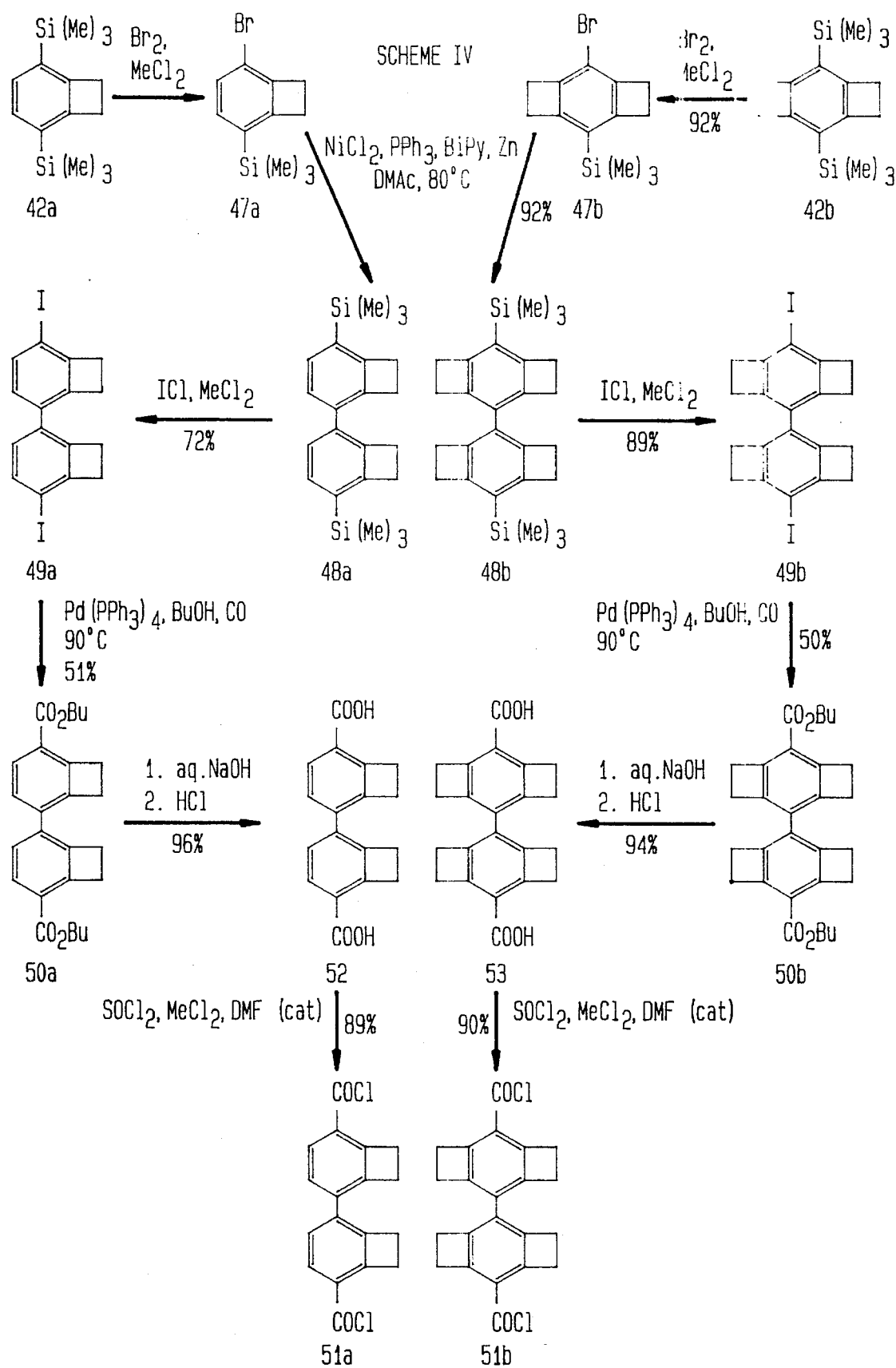
FIG. 11 is a preparatory scheme for making difunctional bitricyclodecatriene monomers, specifically [2,2'-bidicyclo[2.4.0]octa-1,3,5-triene]- 5,5'-dicarboxylic acid (BXTA) and [2,2'-bitricyclo[6.2.0.0]deca-1,3,(6),7-triene]-7, 7'-dicarboxylic acid.

Another embodiment of the present invention is illustrated in the preparatory scheme of FIG. 11. FIG. 11 shows a method of making the difunctional bitricyclodecatriene monomers, compounds 52 and 53, which are [2,2'-bidicyclo[2.4.0[octa-1,3,5-triene]-5,5'-dicarboxylic acid (BXTA) and [2,2'-bitricyclo[6.2.0.0]deca-1,3,(6),7-triene]-7,7'-dicarboxylic acid (QXTA), respectively.

Referring to FIG. 11, the disilylated compounds 42a,b are converted to unsymmetrical monobromide-mono(trimethysiyl) adducts, compounds 47a,b. The unsymmetrical monobromidemono(trimethysiyl) adducts are converted to the diphenyl compounds 48a,b by nickel-catalyzed coupling. A series of recrystallizations remove the statistical symmetric by-products to yield purified unsymmetrical adducts compounds 47a,b. Compounds 47a,b are coupled with a Ni$^0$ catalyst which is formed in situ from metallic zinc and triphenylphosphine/2,2'-bipyridyl ligands in dry dimethylacetamide solvent at 85° C. under an inert atmosphere. The coupled biphenyl silylated products, compounds 48a,b, are separated from the catalyst mixture by precipitation, followed by extraction and filtration through a plug of silica gel. The coupled biphenyltrimethylsilyl compounds 48a,b are converted to the corresponding biphenyl-diiodides compounds 49a,b, preferably with ICl.

The biphenyl-diiodide compounds 49a,b are converted to the respective diacid compounds 52 (BXTA) and 53 (QXTA) by low-temperature lithiation followed by $CO_2$ quench. For larger scale reactions, a palladium-catalyzed CO-insertion technique, to form the dibutyl esters, compounds 50a,b, is preferred. Hydrolysis in a basic methanol-water mixture, followed by acid workup, affords the diacids (compounds 52 and 53) in quantitative yield. The corresponding bis(acid-chloride), compounds 51a,b, are prepared with thionyl chloride and purified by sublimation.

The method steps of the preparatory scheme of FIG. 11 are described in more detail below:

3-Bromo-6-trimethylsilylbenzo[1,2:4,5]dicyclobutene (compound 47b)

Unsymmetrical compound 47b, is prepared in the same manner as dibromide compound 43b above. However, in this instance, only one molar equivalent of bromine is used. The combined extracts were dried over $MgSO_4$ and concentrated on a vacuum line to afford 98% pure white solid 3-bromo-6-trimethylsilylbenzo[1,2:4,5]dicyclobutene (92% yield). Recrystallization from methanol affords glistening white plates. $^1$H NMR (300 MHZ, $CDCl_3$): $\delta$3.07 (s,4H); 3.05 (s,4H); 0.23 (s, 9H). A similar procedure, starting with compound 43a, yielded 3-bromo-6-trimethylsilylbenzocyclobutene (compound 47a). $^1$H NMR (300 MHZ, DMSO-$d_6$): $\delta$3.37 (s,8H).

7,7'-bis(Trimethylsilyl)-2,2'-dibenzodicyclobutene (compound 48b)

The biphenyl compound is prepared in a nickel catalyzed reaction according to the work of Colon, et al., J. Org, Chem,, Vol. 51, pp. 2627–2637 (1986). A sidearm flask is charged with 0.05 g $NiCl_2$ (0.36 mMol, Alfa Aesar, *.*), 1.39 g 325 mesh Zn (21.3 mMol, Cerac Inc., *.*), 0.567 g triphenylphosphine (2.16 mMol, recrystallized from hexane), 0.056 g freshly sublimed 2,2'-bipyridyl (0.36 mMol), and 1.92 g of compound 47b (7.11 mMol). Dry N,N-dimethylacetamide is then added to the flask (approximately 15 ml). The flask is closed to the atmosphere and stirred at 70° C. The typical deep red catalyst formation is visible in less than 3 minutes. The reaction is continued for 1 hour at 70° C. and then removed from the heat. Addition of methanol (20 ml) followed by water (10 ml) causes precipitation of the product. The product and zinc are filtered and washed with methanol. A new filtrate flask is substituted and the solids are washed with petroleum ether, dissolving the product. The solution is dried and removal of the solvent affords the coupled product without a trace of triphenylphosphine (purity 99% per GC; 920 mg, 64.3% yield). The remainder of the product must be extracted from the alcoholic solution with hexane. The hexane is separated and washed with brine, run through a silica gel plug, dried over $MgSO_4$, and concentrated on a vacuum line to give a white crystalline solid, 7,7'-bis(trimethylsilyl)-2,2'-dibenzodicyclobutene, mp 189°–190° C. (combined yield 92%). $^1$H NMR (400 MHZ, $CDCl_3$): $\delta$3.21 (d,8H); 3,17 (d, 8H); 0.29 (s, 18H). A similar procedure, starting with compound 47a, resulted in 5,5'-bis(trimethylsilyl)-2,2'-dibenzocyclobutene (compound 48a). $^1$H NMR (300 MHZ, $CDCl_3$): $\delta$7.43 (d of d, 4H); 3.42 (t, 4H); 3.28 (t, rH); 0.30 (s, 18H).

Dibutyl-2,2'-dibenzodicyclobutene-7,7'-dicarboxylate (compound 50b)

The biphenyl diester is prepared from the corresponding diiodide (compound 49b) using Pd-catalyzed carbonylation at elevated CO pressures is hot butanol, as previously described in the production of 3,6-diesters of benzocyclobutene. The product is recrystallized from a butanol/methanol mixture, mp 183°–185° C. $^1$H NMR (360 MHZ, $CDCl_3$): $\delta$4.28 (t,4H); 3.34 (s, 8H); 3.22 (s, 8H); 1.73 (q, 4H); 1.50 (m, 4H); 0.98 (s, 6H). A similar procedure starting with compound 49a, resulted in dibutyl-2,2'-dibenzocyclobutene-5,5'-dicarboxylate (compound 50a), mp 133°–134° C.; $^1$H NMR (360 MHZ, $CDCl_3$): $\delta$7.88 (d, 2H); 7.56 (d, 2H); 3.47 (s, 8H); 1.76 (m, 4H); 1.49 (m, 4H); 0.99 (t,6H), $^1$H NMR (360 MHZ, benzene-$d_6$): $\delta$7.46 (d,2H); 7.16 (solvent); 4.22 (t,4H); 3.28 (t,4H); 1.29 (m4H); 0.82 (t,6H).

The diacid compounds 52 and 53 are obtained by hydrolyzing the diester compound 50a,b (2 mMol) in aqueous NaOH solution (10 ml 10%) at reflux, recovering the diacid precipitate by acidification and drying under vacuum.

2,2'-Dibenzodicyclobutene-7,7'-dicarboxylic acid dichloride (compound 51b)

The diacid compound 53 is suspended in dichloromethane. Thionyl chloride (5 mmol) is then added to the suspension. A small amount of DMF is added as a phase-transfer catalyst and the mixture is heated to reflux with a condenser and drying tube attached. The complete acid chloride formation is evident by disappearance of cloudiness in the mixture, and verified by GC-MS analysis. The mixture is filtered hot, the solvents are removed, leaving a yellow solid mass. The yellow solid mass is transferred to a sublimation chamber, and the product is effectively sublimed onto a cold finger at –78° C. in an oil bath at 170° C. The recovered product is 99% pure white powder. $^1$H NMR (360 MHZ, $CDCl_3$): $\delta$3.42 (s,8H); $\delta$3.24 (s,8H). The acid dichloride, 2,2'-dibenzocyclobutene-5,5-dicarboxylic acid dichloride (compound 51a), was derived from aliacid compound 52. $^1$H NMR (360 MHZ, $CDCl_3$): $\delta$7.91 (d,2H); 7.62 (d,2H); 3.59 (t,4H); 3.50 (t,4H).

Improved material properties can be achieved by increasing the density of crosslinkable functionalities by use of the difunctional bitricyclodecatriene monomers of the present invention wherein two cyclobutabenzene molecules have been coupled in a biphenyl fashion while retaining the para-orientation of the functional acid groups. When a polymer containing the difunctional bitricyclodecatriene monomers is subjected to a temperature sufficient to initiate cross-linking, the density of crosslinking moiety will be two- or fourfold greater. Further, as a result of the conformation of such biphenyl structures, the direction of the increased crosslinking reactions will have to acquire higher dimensionality. Rather than the two-dimensional flat sheets obtained with a single crosslinking functionality, the biphenyl species will provide a third dimension of reactivity, thus rendering a higher density crosslinked polymer. The higher density crosslinked polymer will have improved material properties such as strength, modulus, toughness, and flame resistance.

As demonstrated above, the monomers XTA and DXTA have been successfully incorporated into PPTA copolymers at various concentrations while maintaining those properties of a PPTA polymer which are essential for processing. These properties include the high aspect ratio (uniaxial shape) necessary for lyotropic liquid crystalline behavior. Similar results have been obtained with the monomers BXTA and QXTA.

Figure 12:
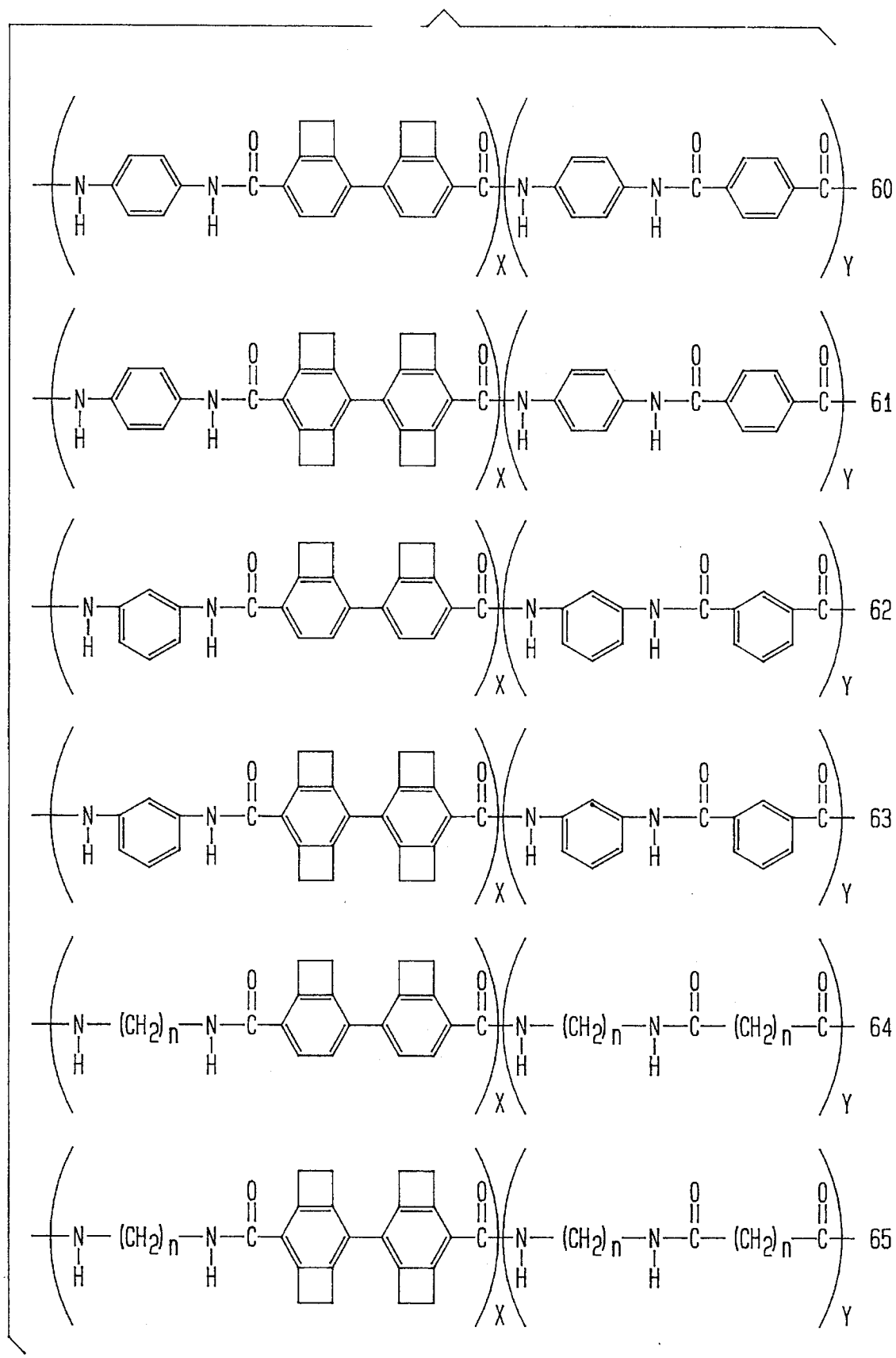
FIG. 12 illustrated various copolymer structures incorporation BXTA and QXTA in accordance with the principles of the invention.

In specific illustrative embodiments shown in FIG. 12, copolymers of the difunctional bitricyclodecatriene monomers BXTA and QXTA were made by standard condensation reactions with arylamines, such as PPTA (compounds 60 and 61, respectively) or poly(m-phenylene terephthalamide) (PMTA or Nomex®, a trademark of Dupont Chemical Company, Wilmington, Del.) (compounds 62 and 63, respectively); or akylamines, such as Nylon (compounds 64 and 65, respectively). Typical low temperature solution condensation reactions used a 1:1 molar ratio of monomers in solvent, such as NMP:HMPA (PPTA) or NMP (preferred for PMTA)

Upon heat treatment, in excess of 250° C., crosslinking of the BXTA or QXTA-containing homo- or copolymers will result in three-dimensional strengthening and a high performance polymer having improved material properties such as strength, modulus, toughness, and flame resistance.

Although the invention has been described in terms of specific embodiments and applications, persons skilled in the art can, in light of this teaching, generate additional embodiments without exceeding the scope or departing from the spirit of the claimed invention. Accordingly, it is to be understood that the drawing and description in this disclosure are proffered to facilitate comprehension of the invention, and should not be construed to limit the scope thereof.

What is claimed is:

1. A resin which is a reaction product by polymerization or copolymerization of monomers of the general formula:

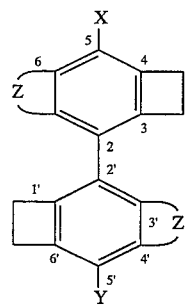

wherein Z is hydrogens or a cyclobutane ring; and X and Y are carboxyl, amino, alcohol, isocyanate, acid halide, or 4-halobenzoyl groups.

2. The resin of claim 1 which is prepared by copolymerization of [2,2'-bidicyclo[2.4.0]octa-1,3,5-triene]-5,5'-dicarboxylic acid with an aromatic diamine.

3. The resin of claim 1 which is prepared by copolymerization of [2,2'-bitricyclo[6.2.0.0]deca-1,3,(6),7-triene]-7,7'-dicarboxylic acid with an aromatic diamine.

4. The resin of claim 1 which is prepared by copolymerization of 2,2'-bidicyclo]2.4.0]octa-1,3,5-triene]-5,5'-dicarboxylic acid with an aliphatic diamine.

5. The resin of claim 1 which is prepared by copolymerization of [2,2'-bitricyclo[6.2.0.0]deca-1,3,(6),7-triene]-7,7'-dicarboxylic acid with an aliphatic diamine.

6. The resin of claim 1 which is crosslinked by heating the reaction product to a temperature in excess of 250° C.

* * * * *